United States Patent
Shimizu

(10) Patent No.: US 8,940,932 B2
(45) Date of Patent: Jan. 27, 2015

(54) PROCESS FOR PRODUCING ACETIC ACID

(75) Inventor: Masahiko Shimizu, Tokyo (JP)

(73) Assignee: Daicel Corporation, Osaka-shi (JP)

( * ) Notice: Subject to any disclaimer, the term of this patent is extended or adjusted under 35 U.S.C. 154(b) by 169 days.

(21) Appl. No.: 13/825,266

(22) PCT Filed: Sep. 27, 2011

(86) PCT No.: PCT/JP2011/072059
§ 371 (c)(1),
(2), (4) Date: Mar. 20, 2013

(87) PCT Pub. No.: WO2012/046593
PCT Pub. Date: Apr. 12, 2012

(65) Prior Publication Data
US 2013/0303800 A1 Nov. 14, 2013

(30) Foreign Application Priority Data
Oct. 6, 2010 (JP) ................................ 2010-226664

(51) Int. Cl.
*C07C 51/12* (2006.01)
*C07C 51/44* (2006.01)

(52) U.S. Cl.
CPC ................. *C07C 51/12* (2013.01); *C07C 51/44* (2013.01)
USPC ....................................................... 562/519

(58) Field of Classification Search
None
See application file for complete search history.

(56) References Cited

U.S. PATENT DOCUMENTS

| | | | |
|---|---|---|---|
| 4,766,258 | A | 8/1988 | Komatsu et al. |
| 5,625,095 | A | 4/1997 | Miura et al. |
| 6,143,930 | A | 11/2000 | Singh et al. |
| 6,458,996 | B1 | 10/2002 | Muskett |

FOREIGN PATENT DOCUMENTS

| | | | |
|---|---|---|---|
| EP | 2 653 458 A1 | 10/2013 | |
| JP | 61-267533 A | 11/1986 | |
| JP | 63-290835 A | 11/1988 | |
| JP | 4-266843 A | 9/1992 | |
| JP | 8-67650 A | 3/1996 | |
| JP | 2001-300203 A | 10/2001 | |
| JP | 2007-224040 A | 9/2007 | |
| JP | 2010-106045 A | 5/2010 | |

OTHER PUBLICATIONS

Extended European Search Report issued Sep. 11, 2014, in European Patent Application No. 11830526.7.
Faanes, A. and S. Skogestad., "Buffer Tank Design for Acceptable Control Performance," Industrial & Engineering Chemistry Research (Apr. 8, 2003), vol. 42, No. 10, pp. 2198-2208.
International Search Report, issued in PCT/JP2011/072059, dated Jan. 31, 2012.
English translation of International Preliminary Report on Patentability and Written Opinion issued May 16, 2013, in PCT International Application No. PCT/JP2011/072059.

*Primary Examiner* — Yevegeny Valenrod
(74) *Attorney, Agent, or Firm* — Birch, Stewart, Kolasch & Birch, LLP

(57) ABSTRACT

A process for stably producing high purity acetic acid comprising a condensation step for condensing and temporarily holding the lower boiling component in a decanter and discharging from the decanter; and a step for separating the lower boiling component discharged from the decanter into acetaldehyde and a liquid residue and recycling the liquid residue to the reaction system. In the condensation step, the amount of the lower boiling component to be held is controlled based on the fluctuating flow rate of the lower boiling component to be fed to the decanter.

14 Claims, 2 Drawing Sheets

PROCESS FOR PRODUCING ACETIC ACID

TECHNICAL FIELD

The present invention relates to a process for stably producing acetic acid by carbonylation of methanol in the presence of a metal catalyst (such as a rhodium catalyst) and methyl iodide.

BACKGROUND ART

Various industrial production processes of acetic acid have been known. Among others, an industrially excellent process includes a process which comprises continuously allowing methanol to react with carbon monoxide with the use of a rhodium catalyst and methyl iodide in the presence of water to give acetic acid. Moreover, recently improvement in reaction conditions and catalysts was investigated, and an industrial process for producing acetic acid with a highly efficient production has been developed by addition of a catalyst stabilizer (such as an iodide salt) and the reaction under a low water content condition compared with the conventional condition. This process enables by-products including carbon dioxide or propionic acid to be reduced because of lowered water content in the reaction mixture. In the reaction mixture, however, there are by-products (impurities) in minor quantities other than these components, for example, a carbonyl compound (e.g., acetaldehyde, butyraldehyde, crotonaldehyde, 2-ethylcrotonaldehyde, and an aldol condensation product thereof), an organic iodide (e.g., an alkyl iodide other than methyl iodide, such as ethyl iodide, butyl iodide, or hexyl iodide). As the production of acetic acid increases, the production of the impurities increases, which deteriorates the quality of acetic acid. For example, in a quality test by which the very minute amounts of the reducing impurities present in acetic acid are checked, which is called a permanganate-reducing substance test (permanganate time), impurities having very slight concentrations, which are hard to quantitatively determine even with today's highly advanced instrumental analysis, can be detected, and these impurities lead to deterioration of product quality. Moreover, some of these impurities exert a bad influence in connection with use of acetic acid. For example, in a process for producing vinyl acetate from ethylene and acetic acid, it is known that the impurities deteriorate a palladium-series catalyst used in the process.

Unfortunately, the carbonyl compound or the alkyl iodide is hard to remove sufficiently by ordinary means, such as distillation, because the boiling point of the carbonyl compound or the alkyl iodide is close to a boiling point of an iodide catalyst accelerator, or other reasons.

Thus, for example, the treatment of crude acetic acid containing these minute impurities with ozone or an oxidizing agent has been developed. Because the treatment has the limitation on the concentrations of impurities to be treated, the carbonyl compound and the organic iodide cannot be removed efficiently.

Meanwhile, in a continuous reaction process, removal of a carbonyl compound in a process circulation liquid is also being attempted. For example, Japanese Patent Application Laid-Open Publication No. 4-266843 (JP-4-266843A, Patent Document 1) discloses a process for removing a carbonyl impurity, which comprises allowing a methyl iodide stream to be recycled to a carbonylation reactor to contact with an amino compound that is allowed to react with a carbonyl impurity to form a water-soluble nitrogenous derivative, separating the resulting organic methyl iodide phase from the resulting aqueous derivative phase, and distilling the methyl iodide phase. The concentration of the carbonyl impurity in the organic stream to be recycled to the carbonylation reactor is still high, and it is difficult to remove the carbonyl impurity sufficiently. Moreover, the process described in this patent document requires removal of the nitrogenous compound.

Japanese Patent Application Laid-Open Publication No. 8-67650 (JP-8-67650A, Patent Document 2) discloses a process for producing high-purity acetic acid, comprising allowing methanol to continuously react with carbon monoxide in the presence of a rhodium catalyst, an iodide salt, and methyl iodide, wherein the reaction is carried out by removing acetaldehyde from a process liquid being circulated into a reactor to maintain the acetaldehyde concentration in the reaction mixture at 400 ppm or lower. This patent document forcuses attention on that most of the impurities are formed in the reaction system and the formation of such impurities is due to the by-product acetaldehyde produced in the reaction system. Therefore, the concentration of acetaldehyde in the reaction system is reduced to decrease the carbonyl compound or the organic iodide, and, as s result, high-purity acetic acid can be obtained.

In addition, this patent document discloses, relating to a process for producing acetic acid while removing acetaldehyde, that the process comprises separating the reaction mixture into a volatile phase containing acetic acid, methyl acetate and methyl iodide and a low-volatile phase containing the rhodium catalyst, distilling the volatile phase to obtain a product mixture containing acetic acid and an overhead containing methyl acetate and methyl iodide, and recirculating the resulting overhead into the reactor, wherein the overhead or a carbonyl impurity (particularly acetaldehyde) condensate thereof is allowed to contact with water to separate an organic phase containing methyl acetate and methyl iodide and an aqueous phase containing the carbonyl impurity, and the organic phase is recirculated into the reactor. Moreover, this document discloses that a concrete method for obtaining methyl iodide from the carbonyl impurity condensate preferably includes a method which comprises separating an acetaldehyde liquid containing methyl iodide from the process liquid by distillation, and selectively extracting the resulting acetaldehyde liquid with water.

Incidentally, this document does not disclose that the flow rate of the overhead is controlled in recirculating the overhead into the reactor.

RELATED ART DOCUMENTS

Patent Documents

Patent Document 1: JP-4-266843A (Claims)
Patent Document 2: JP-8-67650A (Claims)

SUMMARY OF THE INVENTION

Problems to be Solved by the Invention

It is therefore an object of the present invention to provide a process for stably producing acetic acid while efficiently removing acetaldehyde.

Another object of the present invention is to provide a process for producing acetic acid while recycling methyl iodide as a catalyst with a high efficiency.

Means to Solve the Problems

In a series of continuous acetic acid production processes with a catalyst system containing a metal catalyst, a halide salt and methyl iodide, the inventor of the present invention investigated a process for removing acetaldehyde from a lower boiling point component (an overhead) which is obtained of ter separation of a stream containing acetic acid and at least contains methyl iodide and acetaldehyde, collecting a useful component (such as methyl iodide) efficiently, and recycling the useful component to the reaction system or others. The inventor found that direct removal of acetaldehyde from the overhead by distillation or other means actually made it difficult to stably operate the process.

Specifically, in order to remove acetaldehyde from the overhead, the following steps are required: the overhead is condensed and temporarily retained in a decanter, and further the condensed overhead (or overhead condensate) is fed from the decanter to an acetaldehyde separation process (for example, a distillation process). Through the series of continuous production steps, the flow rate of the overhead fed to the decanter usually fluctuates with the pressure fluctuation in the process. However, since the decanter has an allowable capacity limit, direct feeding of the overhead causes the fluctuation of the liquid level in the decanter with the flow rate fluctuation of the overhead, and the fluctuation of the liquid level sometimes hinders stable operation of the process depending on the extent of the fluctuation. In contrast, an attempt to feed the acetaldehyde separation process with the overhead so as to correspond to the flow rate fluctuation thereof for the purpose of reducing the fluctuation of the liquid level in the decanter cannot sufficiently ease (or absorbs) the flow rate fluctuation of the overhead fed from the decanter in the acetaldehyde separation process. Thus, the separation of acetaldehyde is sometimes insufficient (whereby the concentration of acetaldehyde in the reaction system is increased), or an acetaldehyde separation apparatus (such as a distillation column) sometimes fails to be operated stably. Moreover, since the flow rate fluctuation of the overhead cannot be moderated in the acetaldehyde separation process, the liquid level in the decanter (further the pre-step) fluctuates after all.

Accordingly, the inventor of the present invention made intensive studies to achieve the above objects and finally found that, by (i) circulating part (a portion) of the condensed overhead to be fed to the decanter to the reaction system without sending to the acetaldehyde separation process or (ii) feeding the overhead from the decanter to the acetaldehyde separation process through the buffer tank, the amount of the overhead to be stored in the decanter is adjusted or controlled depending on the fluctuation of the feed amount of the overhead, and then the amount of the overhead to be fed from the decanter to the acetaldehyde separation process is adjusted or controlled; in this manner, a series of acetic acid production processes, comprising removing acetaldehyde and collecting methyl iodide, is carried out stably and efficiently. The present invention was accomplished based on the above findings.

That is, the present invention includes a process (a closed process) for producing acetic acid, which comprises the following steps: a reaction step for continuously allowing methanol to react with carbon monoxide in the presence of a catalyst system comprising a metal catalyst (e.g., a rhodium catalyst), a halide salt (e.g., an iodide salt), and methyl iodide in a carbonylation reactor; a flash evaporation step for continuously feeding a flasher (or an evaporator) with a reaction mixture from the reactor and separating a lower boiling point component (2A) (or a volatile component (2A)) containing product acetic acid and methyl acetate and a higher boiling point component (2B) (or a low-volatile component (2B)) containing the metal catalyst and the halide salt; an acetic acid collection step for continuously feeding a distillation column with the lower boiling point component (2A), and separating a lower boiling point component (or an overhead or a first overhead) (3A) containing methyl iodide and by-product acetaldehyde and a stream (3B) containing acetic acid to collect acetic acid; a condensation step for condensing (condensing by cooling) and temporarily holding (storing) the lower boiling point component (3A) (or part of all of the lower boiling point component (3A)) in a decanter (a decanter apparatus, a storage vessel) [or holding the condensed component (condensate)] and discharging the lower boiling point component (3A) from the decanter [or discharging the lower boiling point component (3A) for feeding the component (3A) to a separation and recycling step or subjecting the component (3A) to acetaldehyde separation]; and a separation and recycling step for separating the condensed lower boiling point component (3A) [or the lower boiling point component (3A) discharged from the decanter] [or a condensed component (3A') in the lower boiling point component (3A)] into acetaldehyde and a liquid residue (or residual liquid) and recycling (or circulating) the liquid residue, e.g., recycling to at least one step from the reaction step (or the reactor or the reaction system) to the acetaldehyde-separation step; wherein in the condensation step, the amount to be held of the lower boiling point component (3A) [or the condensed component (3A') in the lower boiling point component (3A)] is adjusted or controlled based on a fluctuating flow rate of the lower boiling point component (3A) [or the condensed component (3A') in the lower boiling point component (3A)] to be fed to the decanter.

According to the production process of acetic acid, the amount of the lower boiling point component (3A) to be fed to the decanter significantly fluctuates in the process operation (or throughout the whole process). For example, with respect to the fluctuation (or change or variation), assuming that the average flow rate of the lower boiling point component (3A) to be fed to the decanter is 100 in terms of liquid (condensate) volume, the flow rate of the lower boiling point component (3A) to be fed to the decanter may be about 80 to 120 in the process operation.

A concrete method for adjusting (or controlling) the amount of the lower boiling point component (3A) to be held includes, for example, (1) a method in which the lower boiling point component (3A) is discharged so that the fluctuation of the amount or liquid level of the lower boiling point component (3A) to be held in the decanter may be inhibited (or substantially kept constant) and/or (2) a method in which a decanter having a buf fering function is used as the decanter to ease (or dif fuse) the fluctuation of the amount of the lower boiling point component (or condensate) (3A) fed inside the decanter.

According to the method (1), for example, in the condensation step, assuming that each of the average liquid level (or average amount) and the average interface level of the lower boiling point component (3A) to be held in the decanter is 100, the liquid level (or average amount) and/or interface level of the lower boiling point component (3A) to be held in the decanter may be adjusted [specifically, the lower boiling point component (3A) may be discharged from the decanter to adjust the liquid level] to about 90 to 110 (for example, about 95 to 105) in the process operation. The liquid level means a height of the contact surface of the condensed lower boiling point component (3A) with gas (gas phase) in the decanter. When the condensed lower boiling point component (3A) is separated into two phases (upper phase and lower phase), the interface level means a height of the boundary between two phases (or a height of the lower phase). Thus the concept of the interface level is used when the lower boiling point component (3A) undergoes layer separation (phase separation).

Moreover, according to the method (2), in the condensation step, a decanter having a buffering function may be used as the decanter. In particular, the retention time (or holding time) of the lower boiling point component (3A) [or the condensed component (3A') in the lower boiling point component (3A)] in such a decanter may be regulated so as to be not less than 1 minute (e.g., not less than 3 minutes). Use of the decanter which allows such a sufficient retention time can efficiently ease the flow rate fluctuation of the lower boiling point component (3A) [or the condensed component (3A') in the lower boiling point component (3A)] in the decanter.

According to the present invention, in order to carry out the whole process stably, in the condensation step the amount of the lower boiling point component (3A) to be held may usually be adjusted or controlled based on the fluctuation of the flow rate of the lower boiling point component (3A) to be fed to the decanter, and further the amount of the lower boiling point component (3A) [or the condensed component (3A') in the lower boiling point component (3A)] to be fed to the separation and recycling step may be adjusted or controlled. Specifically, in the condensation step, the amount of the lower boiling point component (3A) to be fed to the separation and recycling step may be adjusted so as to be constant or almost constant (or substantially be kept constant) [for example, assuming that the average flow rate of the lower boiling point component (3A) is 100, the flow rate of the lower boiling point component (3A) to be fed to the separation and recycling step may be adjusted to 90 to 110 (for example, 95 to 105) in the process operation].

Representative examples of the method for adjusting or controlling the amount of the lower boiling point component (3A) to be fed to the separation and recycling step include at least one selected from the following methods (a), (b), and (c): (a) a method for circulating part of the lower boiling point component (3A) discharged from the decanter to a step different from the separation and recycling step [for example, at least one selected from the group consisting of the reaction system (reactor or reaction step) and the acetic acid collection step (or distillation column), particularly at least the reaction system (or reactor) or reaction step]; (b) a method for feeding the separation and recycling step with the lower boiling point component (3A) discharged from the decanter through a storage vessel having a buffering function; and (c) a method for adjusting the amount of the lower boiling point component (3A) to be discharged from the decanter to keep constant (or almost constant, for example, assuming that the average flow rate of the lower boiling point component (3A) to be discharged from the decanter is 100, the amount of the lower boiling point component (3A) to be discharged from the decanter in the process operation is adjusted to 90 to 110 (for example, 95 to 105)).

For the method (a), in the condensation step, the amount (or flow rate) of the lower boiling point component (3A) to be fed to the separation and recycling step may be adjusted by circulating part of the lower boiling point component (3A) discharged from the decanter to a step different from the separation and recycling step. In the method (a), not less than 10%, preferably not less than 20% (for example, about 20 to 90%), of the average flow rate of the lower boiling point component (3A) to be fed to the decanter may be circulated (or recycled), in particular, not less than 40% (for example, about 40 to 90%) of the average flow rate may be circulated. Moreover, in the method (a), the lower boiling point component (3A) may be separated into an upper layer and a lower layer in the decanter, and the upper layer and/or the lower layer may be circulated. Further, the lower boiling point component (3A) may be circulated as a single phase without separation of the lower boiling point component (3A) into two layers.

For the method (b), the retention time of the lower boiling point component (3A) in the storage vessel having a buffering function may be not less than 0.5 minutes (for example, not less than 1 minute). Moreover, in the method (b), the total time of the retention time of the lower boiling point component (3A) in the decanter and the retention time of the lower boiling point component (3A) in the storage vessel may be not less than 1.5 minutes (for example, not less than 2 minutes).

For the method (c), typically, a decanter having a buffering function is used as the decanter, and the retention time of the lower boiling point component (3A) in the decanter may be not less than 1 minute.

The methods (a) to (c) may be carried out alone or in combination (for example, at least the method (a) or the method (b)).

According to the present invention, not only removal of acetaldehyde but also collection (recycling) of methyl iodide is efficiently achieved. For example, the separation and recycling step may comprise feeding the acetaldehyde distillation column with the lower boiling point component (3A), separating a lower boiling point component (4A) (or a second overhead (4A)) containing acetaldehyde and a higher boiling point component (4B) (or a bottom stream (4B)) containing methyl iodide by distillation, and recycling the higher boiling point component (4B) as a liquid residue [for example, at least one member selected from the group consisting of the reaction system (reactor or reaction step), the acetic acid collection step (or distillation column), and the acetaldehyde removal column].

Moreover, according to the present invention, the liquid residue separated in the separation and recycling step may be recycled while reducing the fluctuation of the flow rate of the liquid residue. Specifically, in the separation and recycling step, the liquid residue may be recycled through a storage vessel having a buffering function.

The above-mentioned lower boiling point component (4A) sometimes contains methyl iodide which cannot be separated. Thus, according to the present invention, when the lower boiling point component (4A) also contains methyl iodide, in the separation and recycling step methyl iodide may be collected from the lower boiling point component (4A) for recycling [e.g., for recycling to a step from the reaction system to the acetaldehyde separation, for example, recycled to at least one member selected from the group consisting of the reaction system (reactor or reaction step), the acetic acid collection step (or distillation column), and the acetaldehyde distillation column].

Throughout this description, the term "lower boiling point component (3A)" in the condensation step and the steps following the condensation step means a condensed component (a condensate or a liquid component) in the lower boiling point component (or overhead) (3A) separated in the acetic acid collection step. The condensed component sometimes refers to as the term "condensed component (3A')", "condensate (3A')" or the like to be distinguished from the lower boiling point component (3A).

Effects of the Invention

According to the present invention, acetic acid (acetic acid with a high purity) can stably be produced while efficiently removing acetaldehyde by adjusting the amount of the lower boiling point component to be stored in the decanter in response to the fluctuation of the feed amount of the lower boiling point component containing methyl iodide and acetaldehyde. Moreover, according to the present invention, since acetaldehyde can be separated from the lower boiling point component efficiently and reliably, acetic acid can be produced while highly efficiently recycling the co-catalyst, methyl iodide, separated from the lower boiling point component.

DESCRIPTION OF EMBODIMENTS

Figure 1:
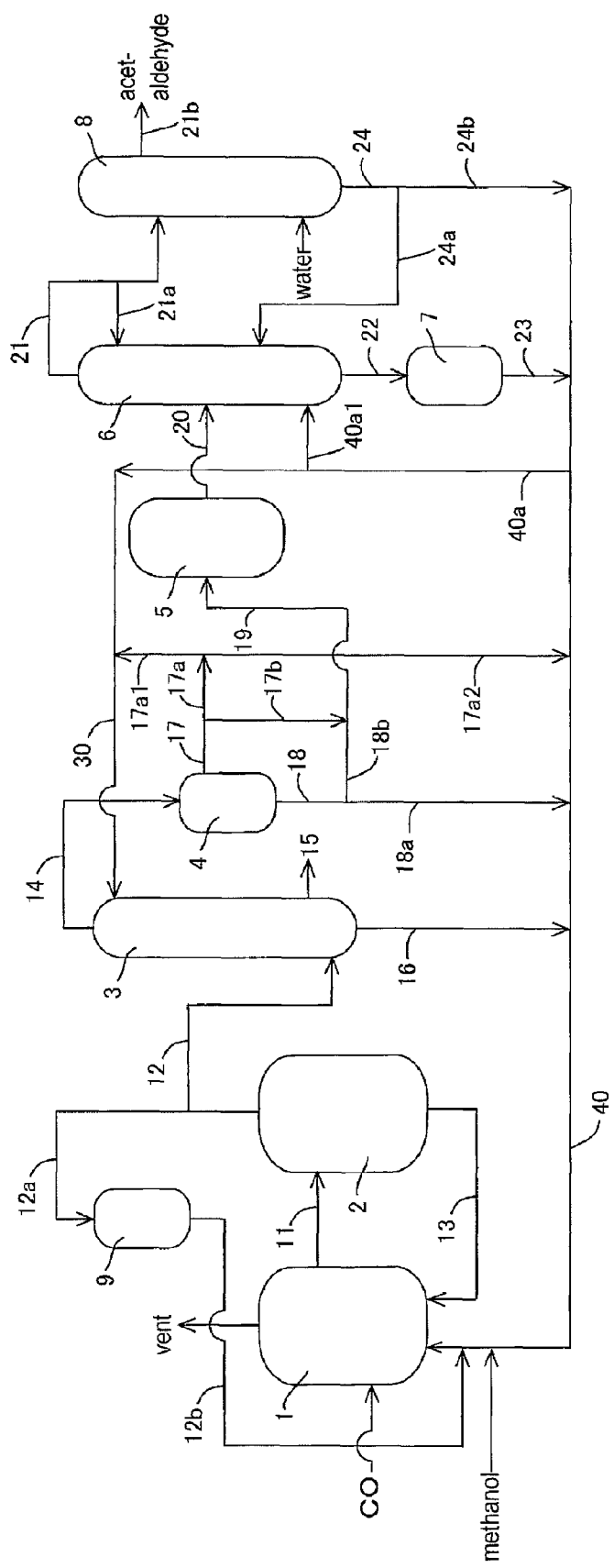
FIG. 1 is a diagram for explaining a production process (or production apparatus) of acetic acid in accordance with an embodiment of the present invention.

Hereinafter, the present invention will be explained in detail with reference to the drawings. FIG. 1 is a diagram (a flow sheet, a schematic process drawing, or a schematic plant layout drawing) for explaining a production process (or production apparatus) of acetic acid in accordance with an embodiment of the present invention.

The embodiment of FIG. 1 shows a continuous process (or apparatus) for producing acetic acid from a liquid reaction medium (or reaction mixture) generated by a continuous carbonylation reaction of methanol with carbon monoxide in the presence of a catalyst system comprising a rhodium catalyst as a metal catalyst and a co-catalyst [lithium iodide as a halide salt and methyl iodide], as well as acetic acid, methyl acetate, and a finite amount of water.

The process (or production apparatus) comprises a reactor (reaction system) 1 for carrying out the carbonylation reaction of methanol; a flasher 2 for separating a lower boiling point component or volatile phase (2A) containing product acetic acid, methyl iodide, methyl acetate, and water and a higher boiling point component or low-volatile phase (2B) containing the rhodium catalyst and lithium iodide from a liquid reaction medium (or a reaction mixture or a reaction solution) which contains acetic acid generated by the reaction; a splitter column 3 for separating a lower boiling point component or overhead (a first overhead) (3A) containing methyl iodide, methyl acetate, by-product acetaldehyde, water, and others, a stream or acetic acid phase (3B) containing acetic acid as a side stream, and a higher boiling point component (3C) containing acetic acid, water, propionic acid, and others, from the lower boiling point component (2A) fed to the flasher 2; a decanter 4 for temporarily holding or storing the lower boiling point component (3A) condensed by cooling [or a condensed component (3A') in the lower boiling point component (3A)]; a buffer tank 5 for temporarily storing (or retaining) the lower boiling point component (3A) [or the condensed component (3A') in the lower boiling point component (3A)] fed or discharged from the decanter 4; a distillation column (an acetaldehyde distillation column) 6 for separating the lower boiling point component (3A) [the condensed component (3A') in the lower boiling point component (3A)] fed or discharged from the decanter 4 or the buffer tank 5 into a lower boiling point component (4A) containing acetaldehyde and methyl iodide and a higher boiling point component (4B) containing methyl iodide, methyl acetate, water, acetic acid, and others; a buffer tank 7 for temporarily storing (or retaining) the higher boiling point component (4B) separated in the distillation column 6; an extraction apparatus or extractor 8 for separating acetaldehyde from the lower boiling point component (4A) by extraction (for example, water extraction) to recycle methyl iodide; and various lines for feeding or circulating each component to these apparatus.

Hereinafter, the process shown in FIG. 1 will be explained in more detail.

To the reactor 1, methanol as a liquid component is continuously fed at a predetermined rate, and carbon monoxide as a gaseous reactant is continuously fed. Moreover, to the reactor 1, a catalyst mixture (liquid catalyst mixture) containing a carbonylation catalyst system [a catalyst system comprising a main metal catalyst component (e.g., a rhodium catalyst) and a co-catalyst (e.g., lithium iodide and methyl iodide)] and water may be fed. Further, a stream (e.g., in the form of liquid) containing lower boiling point component(s) or higher boiling point component(s) from the succeeding step(s) is fed to the reactor 1 through a line 13 and/or a line 40.

Then, inside the reactor 1, a liquid-phase reaction system containing the reactant and the higher boiling point component such as the metal catalyst component (e.g., a rhodium catalyst and lithium iodide) is in equilibrium with a vapor-phase system comprising carbon monoxide, by-products by the reaction (hydrogen, methane, carbon dioxide), and a vaporized lower boiling point component (e.g., methyl iodide, acetic acid as a product, and methyl acetate), and a carbonylation reaction of methanol proceeds. In order to keep the inner pressure of the reactor 1 (e.g., reaction pressure, carbon monoxide partial pressure, and hydrogen partial pressure) constant, a vapor may be withdrawn and discharged from the top of the reactor 1. Further, the vapor withdrawn from the reactor 1 may be cooled by a heat exchanger to give a liquid component (containing acetic acid, methyl acetate, methyl iodide, acetaldehyde, water, and others) and a gaseous component (containing carbon monoxide, hydrogen, and others). The resulting liquid component may be recycled to the reactor 1 (not shown), and the resulting gaseous component (waste gas) may be discharged.

To the reactor 1, if necessary, hydrogen may be fed in order to increase the catalytic activity. Hydrogen may be fed together with carbon monoxide or may be fed separately. Moreover, since the reaction system is an exothermic reaction system that accompanies heat generation, the reactor 1 may be equipped with a heat-removable (or heat-removing) unit or a cooling unit (e.g., a jacket) for controlling a reaction temperature.

Components contained in the reaction mixture (crude reaction liquid) generated in the reactor 1 may include acetic acid, a lower boiling point component or lower boiling point impurity having a boiling point lower than that of acetic acid (e.g., methyl iodide as a co-catalyst, methyl acetate as a reaction product of acetic acid with methanol, and acetaldehyde and a higher iodide (such as hexyl iodide) as by-products), and a higher boiling point component or higher boiling point impurity having a boiling point higher than that of acetic acid [e.g., a metal catalyst component (e.g., a rhodium catalyst), lithium iodide as a co-catalyst, propionic acid, and water].

In order to mainly separate the higher boiling point component (such as the metal catalyst component) from the reaction mixture, part of the reaction mixture is continuously withdrawn from the reactor 1 and introduced or fed into the flasher (distillation column or catalyst separation column) 2 through a feed line 11.

The amount of the reaction mixture to be fed from the reactor 1 to the flasher 2 is not constant and fluctuates (or varies) in the continuous process due to the pressure fluctuation caused by sparging of carbon monoxide to be fed to the liquid phase and others. For example, assuming that the average flow rate of the reaction mixture to be fed to the flasher 2 is 100, the flow rate (or flow velocity, hereinafter, the same applies in the flow rate) of the reaction mixture to be fed to the flasher 2 is about 98 to 102 in the process operation. As described later, for a closed process, the fluctuation of the feed amount affects the succeeding step(s) and is a factor that causes a fluctuation of the feed amount of the lower boiling point component to be fed to the decanter.

In the flasher (flash distillation column) 2, from the reaction mixture, a higher boiling point stream or higher boiling point component or volatile product phase (2B) (mainly containing the metal catalyst component such as the rhodium catalyst or lithium iodide, and others) and a lower boiling point stream or lower boiling point component (2A) (mainly containing acetic acid which is a product and also functions as a reaction solvent, methyl acetate, methyl iodide, water, acetaldehyde, and others) are separated, and the higher boiling point component (2B) is withdrawn from the bottom of the flasher through a bottom line 13 and recycled to the reactor 1, and the lower boiling point component (2A) (acetic acid stream) is withdrawn from the column top or upper part of the flasher 2 through a feed line 12 and fed or introduced to the splitter column (or distillation column) 3. Incidentally, the higher boiling point component (2B) also contains the metal catalyst (the rhodium catalyst) and the halide salt (lithium iodide), and in addition components remaining without evaporation (e.g., methyl iodide, methyl acetate, water, and a trace of acetic acid). The volume proportion of the lower boiling point component (2A) to be separated in the flasher 2 is about 20 to 40% in the whole reaction mixture.

Part of the lower boiling point component (2A) may be heat-removed and recycled to the reactor. In an embodiment of FIG. 1, part of the vaporized lower boiling point component (2A) (for example, about 10 to 30% by volume) is fed to a storage vessel (hold tank) and/or heat exchanger 9 through a line 12a and condensed by heat removal, and recycled to the reactor 1 through a line 12b. In this manner, heat-removal of part of the lower boiling point component (2A) and circulation of the component to the reactor allows an apparatus such as a distillation column (e.g., a splitter column) to be downsized (or miniaturized) even for a large-sized plant. Thus acetic acid can be produced with a high purity and a high yield in a resource-saving and energy-saving equipment.

The amount (feed amount) of the lower boiling point component (2A) to be fed from the flasher 2 to the splitter column 3 also fluctuates in the continuous process with the fluctuation of the amount (feed amount) of the reaction mixture to be fed to the flasher 2. For example, assuming that the average flow rate of the lower boiling point component (2A) to be fed to the splitter column 3 is 100, the flow rate of the lower boiling point component (2A) to be fed to the splitter column 3 is about 98 to 102 in the process operation.

In the splitter column 3, usually, a lower boiling point component (or overhead) (3A) (containing methyl iodide, methyl acetate, acetaldehyde, water, acetic acid, and others) is separated from the column top or upper part of the column through a withdrawing line 14, and a higher boiling point stream or higher boiling point component (3C) (a component containing acetic acid, water, propionic acid, and others) is separated (or removed) from the bottom or lower part of the column through a bottom line 16. The separated higher boiling point component (3C) may be discharged through a line 16, or may partly or wholly be recycled to the reactor 1 through a line 40. A side stream or acetic acid phase stream (3B) (acetic acid stream) mainly containing acetic acid is collected from the splitter column 3 through a feed line 15 by side cut. Incidentally, the stream (3B) containing acetic acid collected by side cut may usually be fed to another distillation column (not shown) through the line 15 and then distilled for purification (not shown). The proportion of the lower boiling point component (3A) to be separated in the splitter column 3 is about 35 to 50% by weight in the total lower boiling point component (2A). As described later, when a process liquid from the succeeding step(s) is circulated or recycled to the splitter column 3, the total amount of the component to be fed from the flasher 12 and the component to be recycled from the succeeding step(s) is subjected to distillation in the splitter column 3 to separate the lower boiling point component (3A).

The amount of the lower boiling point component (3A) to be fed from the splitter column 3 to the decanter 4 is affected by the fluctuation of the amount of the reaction mixture to be fed to the flasher 2 and the fluctuation of the amount of the lower boiling point component (2A) to be fed from the flasher 2 to the splitter column 3, and fluctuates in the continuous process. For example, assuming that the average flow rate of the lower boiling point component (3A) to be fed to the decanter 4 is 100, the flow rate of the lower boiling point component (3A) to be fed to the decanter 4 is about 90 to 110 in the process operation (that is, the flow rate of the lower boiling point component (3A) fluctuates within the range of about 0 to ±10% by volume). The lower boiling point component (3A) is fed to the decanter 4 with such a relatively large fluctuation.

The lower boiling point component (3A) separated through the line 14 is condensed by cooling, continuously fed to the decanter (storage vessel) 4, and temporarily held (stored) in the decanter 4. Inside the decanter 4, the condensed lower boiling point component (condensate) (3A) is sometimes separated into a water-containing upper layer (water layer or water phase) and a lower layer (organic layer or organic phase). When the component (3A) is separated, acetaldehyde and methyl iodide are contained in the both layers. A larger quantity of acetaldehyde is contained in the upper layer (water layer) compared to the lower layer in many cases. In the lower boiling point component (3A) to be fed to the decanter 4, the volume ratio of the upper layer (or upper layer component) relative to the lower layer (or lower layer component) [the former/the latter] is, for example, about 0.5/1 to 1.5/1 (e.g., about 0.7/1 to 1.3/1). The fluctuation of the feed amount in the upper layer and the lower layer is within the same range as that mentioned above.

The lower boiling point component (condensate) (3A) held in the decanter 4 is fed to the acetaldehyde distillation column 6 through a feed line 17 and/or a feed line 18. In the embodiment of FIG. 1, the storage (or the liquid level) of the lower boiling point component (condensate) (3A) to be held in the decanter 4 is significantly restrained from fluctuating by circulating (or recycling) part of the lower boiling point component (3A) to the reaction system or others through a line 17a (sub-line 17a) branched from the line 17 or a line 18a (sub-line 18a) branched from the line 18 based on the flow rate fluctuation of the lower boiling point component (condensate) (3A) to be fed to the decanter 4.

That is, the amount of the lower boiling point component (3A) to be continuously fed to the decanter 4 (for example, the amount to be fed per unit of time) is not constant in the continuous reaction, and as described above, the amount fluctuates through the carbonylation reaction, the flash distillation, and the recycling of the methyl iodide (for example, the amount of the lower boiling point component (3A) to be fed per unit of time is increased or decreased). Accordingly, direct feeding of the lower boiling point component (3A) to the decanter 4 causes large fluctuation of the liquid level of the lower boiling point component (condensate) (3A) condensed and stored in the decanter 4, and the operation of the process is sometimes hindered depending on the extent of the fluctuation. In order to ease (or reduce) the fluctuation, the lower boiling point component (3A) may be fed from the decanter 4 to the acetaldehyde distillation column 6 at a flow rate enough to ease the fluctuation of the flow rate. However, such feeding causes insufficient process in the aldehyde distillation column 6.

Then, in the embodiment of FIG. 1, the amount of the lower boiling point component (condensate) (3A) to be held in the decanter 4 is adjusted or controlled by recycling part of the lower boiling point component (condensate) (3A) to a step (in the embodiment of FIG. 1, the reactor 1 and/or the splitter column 3) different from the separation and recycling step without feeding from the decanter 4 to the distillation column 6 based on the fluctuation of the flow rate of the lower boiling point component (3A) to be fed to the decanter 4.

Specifically, in the embodiment of FIG. 1, the lower boiling point component (condensate) (3A) is discharged from the upper layer and the lower layer in the decanter 4 through the line 17 and the line 18, respectively. The flow rate of the lower boiling point component (condensate) (3A) to be discharged from the decanter 4 is regulated so that each of the liquid levels of the upper layer and the lower layer may be constant (or almost constant) even under the fluctuation of the flow rate of the lower boiling point component (3A) to be fed to the decanter 4. That is, the decanter 4 is provided with liquid level sensors for detecting liquid level fluctuation (not shown), and one of the sensors detects the liquid level fluctuation of the upper layer and the other detects that of the lower layer. The amount of the lower boiling point component (condensate) (3A) to be discharged from the upper layer and the lower layer in the decanter 4 is regulated based on the liquid level information detected by the sensors so that predetermined liquid levels of these layers may be maintained. More specifically, based on the information obtained by the liquid level sensors or other information, when the flow rate to be fed to the decanter is large, the flow rate of the lower boiling point component (condensate) (3A) to be discharged is increased to prevent the liquid level from raising; when the flow rate to be fed to the decanter is small, the flow rate of the lower boiling point component (condensate) (3A) to be discharged is decreased. In such a way, the liquid level of the lower boiling point component (condensate) (3A) in the decanter 4 (the liquid level of the upper layer and that of the lower layer) is kept constant or almost constant by adjusting (controlling) the flow rate in the process operation [for instance, with respect to each of the upper layer and the lower layer, assuming that the average liquid level is 100, the liquid level is regulated (or adjusted) to about 99 to 101 in the process operation, that is, the liquid level fluctuation is adjusted to at most about 1% in the whole process].

Further, a portion of the lower boiling point component (3A) discharged through the line 17 and the line 18 is fed to a line 19 through the line 17b and line 18b. The flow rate of the lower boiling point component (3A) to be fed to the line 19 is adjusted (controlled) to keep constant or almost constant by adjusting the amount of the lower boiling point component (3A) to be circulated through the line 17a and/or the line 18a. That is, in the embodiment of FIG. 1, as described above, the amount of the lower boiling point component (3A) discharged from each of the upper layer and the lower layer in the decanter 4 fluctuates so that the liquid level in the decanter 4 may be constant or almost constant. By changing the amount of the lower boiling point component (3A) to be circulated through the line 17a and/or the line 18a in response to the fluctuation, the flow rate of the lower boiling point component (3A) to be fed to the line 19 is regulated to avoid (or almost avoid) from fluctuating [for instance, assuming that the average flow rate of the lower boiling point component (3A) to be fed to the line 19 is 100 in terms of liquid volume, the flow rate of the lower boiling point component (3A) is regulated (or adjusted) to about 98 to 102 in the process operation, that is, the fluctuation of the flow rate is adjusted to at most about 2% in the whole process]. Incidentally, in the embodiment of FIG. 1, the flow rate fluctuation of the lower boiling point component (3A) to be fed to the line 19 can mainly be controlled by adjusting the amount of the lower boiling point component (3A) to be circulated, and additionally can further be controlled by regulating the retention time of the lower boiling point component (3A) in the decanter 4.

It is sufficient that the flow rate of the lower boiling point component (3A) to be fed to the line 19 is regulated by adjusting the flow rate of the lower boiling point component (3A) to be circulated to the line 17a and/or the line 18a. As far as large fluctuation of the flow rate to be fed to the line 19 is not caused, the flow rate of the lower boiling point component (3A) to be circulated to the line 17a or the line 18a may be kept constant (in other words, the flow rate of the lower boiling point component (3A) to be fed to the line 17b or the line 18b may fluctuate).

Moreover, in the embodiment of FIG. 1, the lower boiling point component (3A) is discharged through the line 17 and the line 18. The flow rate of the lower boiling point component (3A) to be fed to the line 19 may be regulated by discharging the lower boiling point component (3A) through only one of the lines 17 and 18 and circulating part of the lower boiling point component (3A). Further, without reference to the upper layer and the lower layer, the lower boiling point component (3A) may be fed or discharged through a single line.

The lower boiling point component (3A) to be fed to the line 17a may be fed to a line 30 through a line 17a1 and circulated to the splitter column 3, may be fed to a line 40 through a line 17a2 and recycled (or returned) to the reactor 1, or may be recycled through both lines 17a1 and 17a2. Moreover, the lower boiling point component (3A) to be fed to the line 18a is fed to the line 40 and recycled to the reactor 1.

Since the fluctuation of the flow rate of the lower boiling point component (3A) fed to the line 19 is significantly inhibited as described above, the boiling point component (3A) may directly be fed to the distillation column 6. In the embodiment of FIG. 1, in order to further ease (or reduce) the fluctuation of the flow rate, the lower boiling point component (3A) is fed to the distillation column 6 through a storage vessel (buffer tank) 5 having a buffering function. That is, the lower boiling point component (3A) fed to the line 19 is fed to the buffer tank 5 and then fed to the distillation column 6 through a line 20. By temporarily retaining the lower boiling point component (3A) in the buffer tank 5 in such a way, even when the amount to be fed from the buffer tank 5 to the line 20 is kept constant (or almost constant), the fluctuation of the flow rate of the lower boiling point component (3A) fed from the line 19 in the buffer tank 5 can efficiently be eased (or reduced).

In order that the buffer tank 5 may show the function of sufficiently easing the flow rate fluctuation, it is important for the buffer tank 5 to have a capacity enough to retain the lower boiling point component (3A) and to further ease the fluctuation of the flow rate. The capacity depends on the extent of the flow rate fluctuation and may generally be represented in association with the retention time of the lower boiling point component (3A) in the buffer tank 5. The capacity of the buffer tank to the flow rate can generally be adjusted so that the retention time of the lower boiling point component (3A) may be not less than 1 minute (for example, preferably not less than 3 minutes, and more preferably not less than 6 minutes). It is preferable that the buffer tank 5 can retain the lower boiling point component (3A) in the above-mentioned time. As described above, in the case where the flow rate fluctuation of the lower boiling point component (3A) to be fed to the line 17 is suppressed beforehand by recycling the lower boiling point component (3A) or maintaining the sufficient retention time in the decanter as described below, even a buffer tank having a retention time shorter than the above range is capable of operating stably. The retention time (general retention time) can be calculated from the flow rate (or flow velocity) and the capacity of the buffer tank. For example, assuming that the average flow rate of the lower boiling point component (3A) to be fed to the buffer tank 5 is A m³/hour and the average storage amount of the lower boiling point component to be held in the buffer tank 5 is B m³, the retention time can be calculated as (B/A) hours.

The lower boiling point component (3A) fed to the distillation column 6 is separated into a lower boiling point stream or lower boiling point component (or a second overhead) (4A) and a higher boiling point stream or higher boiling point component (4B) in the distillation column 6; wherein the lower boiling point stream (4A) contains a trace of methyl iodide, carbon monoxide, hydrogen, and others in addition to acetaldehyde, and the higher boiling point stream (4B) contains methyl acetate, water, acetic acid, and others.

The separated lower boiling point component (4A) is fed from the column top or upper part to an acetaldehyde extraction apparatus (water extraction column) 8 through a line (discharge line) 21, and acetaldehyde is extracted from the lower boiling point component (4A) using water. The extracted acetaldehyde (aldehyde aqueous solution) is discharged through a line 21b. Incidentally, part of the lower boiling point component (4A) may be returned to the distillation column 6 through a line 21a. Moreover, the raffinate containing a trace of methyl iodide, and others may be discharged out of the system. In the embodiment of FIG. 1, the raffinate discharged through a line 24 is fed to the distillation column 6 through a line 24a, and/or is fed to a line 40 through a line 24b to be recycled to the reactor 1. In such a manner, the distillation or recycling of the raffinate can further improve a recovery percentage of methyl iodide.

Moreover, the separated higher boiling point component (4B) is fed as a liquid residue (bottom fraction or column bottom fraction) through a line 22 to a line 40, leading to the reactor 1 or the splitter column 3. In such a manner, the useful component containing methyl iodide is circulated (recycled) to the reaction system and others. The higher boiling point component (4B) may directly be fed to the line 40 through the line 22. In the embodiment of FIG. 1, the higher boiling point component (4B) is fed to the buffer tank 7 and then to the line 40 through a line 23. That is, although the fluctuation of the flow rate of the higher boiling point component (4B) to be fed through the line 22 is inhibited with the highly controlled flow rate of the lower boiling point component (3A) to be fed to the distillation column 6 as described above, recycling of the raffinate after the acetaldehyde extraction mentioned above, and other factors sometimes cause the flow rate fluctuation of the higher boiling point component (4B). However, even if the flow rate of the higher boiling point component (4B) fluctuates, temporary retention of the higher boiling point component (4B) to be fed through the line 22 in the buffer tank 7 allows the fluctuation in the buffer tank 7 to be eased. Thus the higher boiling point component (4B) can be fed to the line 40 while keeping the flow rate of the higher boiling point component (4B) to be fed to the line 23 constant (or almost constant). Therefore, the flow rate fluctuation of the higher boiling point component (4B) to be recycled can be inhibited (or reduced).

The higher boiling point component (4B) fed to the line 40 may partly or wholly be recycled to the splitter column 3 through a line 40a. The higher boiling point component (4B) fed to the line 40a may partly or wholly be fed to the distillation column 6 through a line 40a1 as far as stable operation of the distillation column 6 can be ensured.

Figure 2:
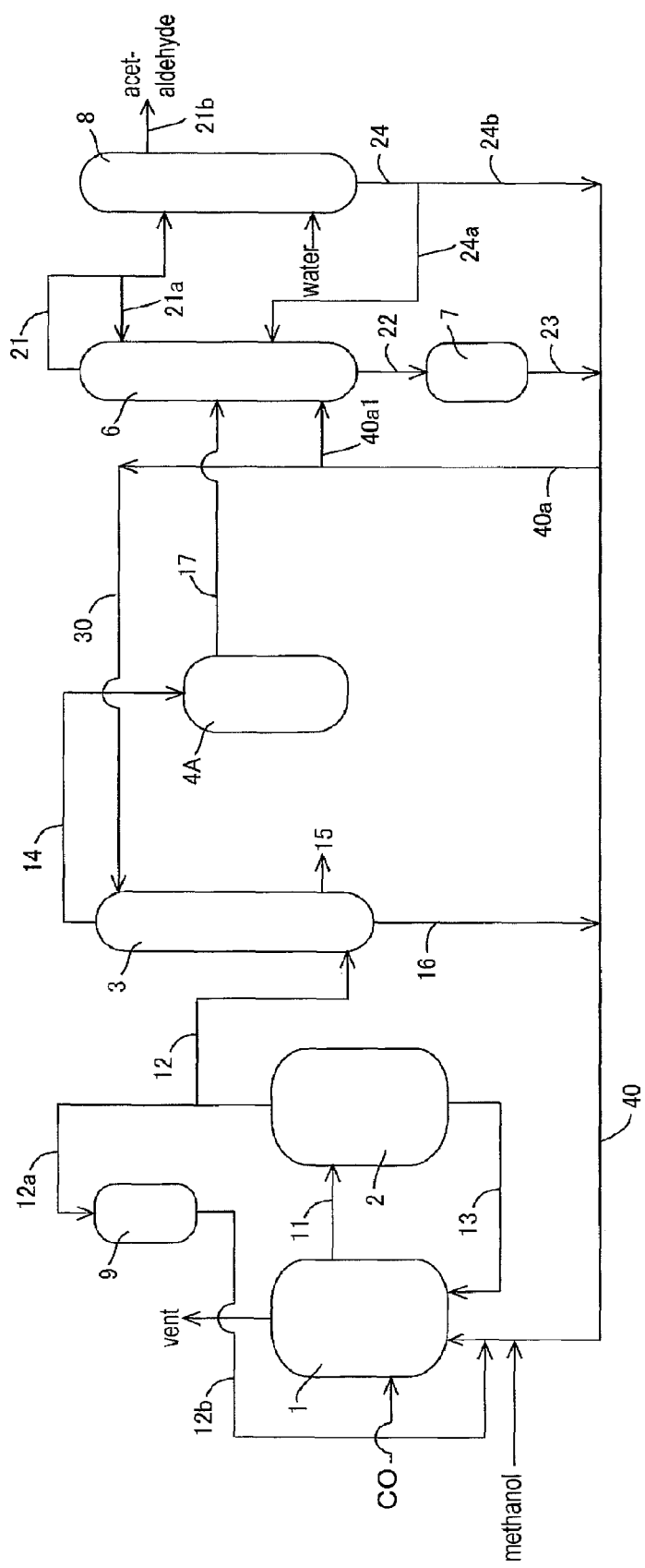
FIG. 2 is a diagram for explaining a production process (or production apparatus) of acetic acid in accordance with another embodiment of the present invention.

FIG. 2 is a diagram for explaining a production process (or production apparatus) of acetic acid in accordance with still another embodiment of the present invention. The process (or apparatus) of FIG. 2 is the same as that of FIG. 1 except that a decanter 4A having a buffering function is used instead of the decanter 4 in FIG. 1 and that the lower boiling point component (3A) is directly fed to the distillation column 6 through the line 17.

That is, as the embodiment of FIG. 1, usually, the decanter cannot fully ease the flow rate fluctuation of the lower boiling point component (3A) to be fed from the splitter column 3. In contrast, in an embodiment of FIG. 2, the decanter 4A having a large capacity enough to ease (reduce) the flow rate fluctuation is used, and the flow rate to be discharged to the line 17 can be kept constant or almost constant by easing the flow rate fluctuation inside the decanter 4A (for instance, assuming that the average flow rate of the lower boiling point component (3A) to be fed through the line 14 is 100 in terms of liquid volume, the flow rate of the lower boiling point component (3A) to be discharged or fed to the line 17 in the process operation can be regulated (or adjusted) to about 98.5 to 101.5, that is, the fluctuation of the flow rate can be adjusted to at most about 1.5%) in the process operation.

Specifically, in the embodiment of FIG. 2, the flow rate of the lower boiling point component (3A) to be discharged from the line 17 (and the line 18) is kept constant or almost constant, whereas in the embodiment of FIG. 1, the flow rate of the lower boiling point component (3A) discharged from the line 17 (and the line 18) is changed. When the flow rate is kept constant, usually the process cannot be operated stably. However, use of the decanter 4A having a sufficient capacity allows stable operation of the process for the following reason: the amount of the lower boiling point component (3A) to be held inside the decanter 4A is fluctuated due to the flow rate fluctuation while the decanter 4A has a capacity enough to ease the fluctuation. In this embodiment, as the same as the embodiment of FIG. 2, the capacity of the decanter 4A is important. The process is stably operable in many cases by adjusting the retention time of the lower boiling point component (3A) inside of the decanter 4A to the same range as described above (for example, not less than 1 minute, preferably not less than 3 minutes, and more preferably not less than 6 minutes).

In the embodiment of FIG. 2, the lower boiling point component (3A) is fed as the upper layer to the distillation column 6 through the line 17. The lower boiling point component (3A) may be fed as the lower layer through the line 18 as shown in the embodiment of FIG. 1, or may be fed through both the line 17 and the line 18. Further, without reference to the upper layer and the lower layer, the lower boiling point component (3A) may be fed through a single line.

(Reaction Step)

In the reaction step (carbonylation reaction system), methanol is carbonylated with carbon monoxide in the presence of the catalyst system. Incidentally, fresh methanol may be fed to the reaction system directly or indirectly, or methanol and/or a derivative thereof withdrawn from various distillation steps may be recycled and fed to the reaction system.

The catalyst system may usually comprise a metal catalyst, a co-catalyst, and an accelerator. Examples of the metal catalyst may include a transition metal catalyst, in particular, a metal catalyst containing the group 8 metal of the Periodic Table (e.g., a cobalt catalyst, a rhodium catalyst, and an iridium catalyst). The catalyst may be an elemental metal or may be used in the form of a metal oxide (including a complex metal oxide), a metal hydroxide, a metal halide (e.g., a chloride, a bromide, and an iodide), a metal carboxylate (e.g., an acetate), a metal salt of an inorganic acid (e.g., a sulfate, a nitrate, and a phosphate), a metal complex, and others. These metal catalysts may be used alone or in combination. The preferred metal catalyst includes a rhodium catalyst and an iridium catalyst (particularly, a rhodium catalyst).

Moreover, it is preferred to use the metal catalyst in the form dissolvable in a liquid reaction medium. Incidentally, since rhodium usually exists as a complex in the liquid reaction medium, the form of the rhodium catalyst is not particularly limited to a specific one as far as the catalyst can change into a complex in the liquid reaction medium, and may be used in various forms. As such a rhodium catalyst, a rhodium iodide complex [for example, $RhI_3$, $[RhI_2(CO)_4]^-$, and $[Rh(CO)_2I_2]^-$], a rhodium carbonyl complex, or the like is particularly preferred. Moreover, the catalyst may be stabilized in the liquid reaction medium by addition of a halide salt (e.g., an iodide salt) and/or water.

The concentration of the metal catalyst is, for example, about 10 to 5000 ppm (on the basis of weight, the same applies hereinafter), preferably about 100 to 4000 ppm, more preferably about 200 to 3000 ppm, and particularly about 300 to 2000 ppm (e.g., about 500 to 1500 ppm) in the whole liquid phase in the reactor.

As the co-catalyst or the accelerator contained in the catalyst system, a halide salt (e.g., an iodide salt) is used. The iodide salt is added in order to stabilize the rhodium catalyst and inhibit side reactions, particularly, in the low water content. The iodide salt is not particularly limited to a specific one as far as the iodide salt produces an iodide ion in the liquid reaction medium. The iodide salt may include, for example, a metal halide [for example, a metal iodide such as an alkali metal iodide (e.g., lithium iodide, sodium iodide, potassium iodide, rubidium iodide, and cesium iodide), an alkaline earth metal iodide (e.g., beryllium iodide, magnesium iodide, and calcium iodide), or an iodide of the group 3B metal of the Periodic Table (e.g., boron iodide and aluminum iodide), corresponding bromide or chloride compounds], an organic halide [for example, an organic iodide such as a phosphonium salt of an iodide (a phosphonium iodide) (e.g., a salt with tributylphosphine and triphenylphosphine) or an ammonium salt of an iodide (an ammonium iodide) (e.g., a salt of tertiary amine, a pyridine compound, an imidazole compound, an imide compound, or the like with an iodide), corresponding bromide or chloride compounds]. Incidentally, the alkali metal iodide (e.g., lithium iodide) also functions as a stabilizer for the carbonylation catalyst (e.g., a rhodium catalyst). These halide salts may be used alone or in combination. Among these halide salts, an alkali metal iodide (such as lithium iodide) is preferred.

In the reaction system (liquid reaction mixture) in the reactor, the concentration of the halide salt (e.g., an iodide salt) is, for example, about 1 to 25% by weight, preferably about 2 to 22% by weight, and more preferably about 3 to 20% by weight in whole liquid phase in the reactor. Further, the concentration of the iodide ion in the reaction system may for example be about 0.07 to 2.5 mol/liter and preferably about 0.25 to 1.5 mol/liter.

As the accelerator contained in the catalyst system, an alkyl iodide (e.g., a $C_{1-4}$alkyl iodide such as methyl iodide, ethyl iodide, or propyl iodide), particularly methyl iodide, is utilized. Since the reaction is promoted at higher concentrations of the accelerator, an economically advantageous concentration can suitably be selected in consideration of the recovery of the accelerator, the plant size of a step for circulating the recovered accelerator to the reactor, the amount of energy necessary for the recovery or circulation, and others. In the reaction system, the concentration of the alkyl iodide (particularly methyl iodide) is, for example, about 1 to 20% by weight, preferably about 5 to 20% by weight, and more preferably about 6 to 16% by weight (e.g., about 8 to 14% by weight) in the whole liquid phase in the reactor.

The reaction is a continuous reaction, and the liquid reaction medium contains methyl acetate. The proportion of methyl acetate may be about 0.1 to 30% by weight, preferably about 0.3 to 20% by weight, and more preferably about 0.5 to 10% by weight (e.g., about 0.5 to 6% by weight) in whole liquid reaction medium.

The carbon monoxide to be fed to the reaction system may be used as a pure gas or may be used as a gas diluted with an inactive gas (e.g., nitrogen, helium, and carbon dioxide). Moreover, exhausted gas component(s) containing carbon monoxide obtained from the succeeding step(s) may be recycled to the reaction system. The carbon monoxide partial pressure in the reactor may for example be about 2 to 30 atmospheres and preferably about 4 to 15 atmospheres.

In the carbonylation reaction, hydrogen is formed (or generated) by a shift reaction between carbon monoxide and water. Hydrogen may be fed to the reaction system. The hydrogen may be fed as a mixed gas with carbon monoxide as a raw material to the reaction system. Moreover, the hydrogen may be fed to the reaction system by recycling gaseous component(s) (including hydrogen, carbonmonoxide, and others) exhausted in the succeeding distillation step(s) (distillation column), if necessary after suitably purifying the gaseous component(s). The hydrogen partial pressure in the reaction system may for example be about 0.5 to 250 kPa, preferably about 1 to 200 kPa, and more preferably about 5 to 150 kPa (e.g., about 10 to 100 kPa) in terms of absolute pressure.

The carbon monoxide partial pressure or hydrogen partial pressure in the reaction system may be adjusted, for example, by suitably adjusting the amount of the carbon monoxide and hydrogen fed and/or recycled to the reaction system, the amount of raw substances (e.g., methanol) fed to the reaction system, the reaction temperature, the reaction pressure, and others.

In the carbonylation reaction, the reaction temperature may be, for example, about 150 to 250° C., preferably about 160 to 230° C., and more preferably about 180 to 220° C. Moreover, the reaction pressure (total reactor pressure), including partial pressures of by-products, may be, for example, about 15 to 40 atmospheres.

The reaction may be carried out in the presence or absence of a solvent. The reaction solvent is not limited to a specific one as far as the reactivity, or the separation or purification efficiency does not decrease, and a variety of solvents may be used. In usual cases, acetic acid as a product may be practically utilized as a solvent.

The concentration of water in the reaction system is not limited to a specific one, and may be a low concentration. The concentration of water in the reaction system is, for example, not more than 15% by weight (e.g., about 0.1 to 12% by weight), preferably not more than 10% by weight (e.g., about 0.1 to 8% by weight), and more preferably about 0.1 to 5% by weight and may usually be about 1 to 15% by weight (e.g., about 2 to 10% by weight) in the whole liquid phase of the reaction system. The solubility of carbon monoxide in the liquid fed to the flasher is decreased by carrying out the reaction while maintaining a specified concentration of each component [particularly, an iodide salt (lithium iodide) and water] in the reaction system, and the loss of carbon monoxide can be reduced.

In the foregoing carbonylation reaction, production of acetic acid is accompanied by production of an ester of the product acetic acid with methanol (methyl acetate), water generated with the esterification reaction, additionally acetaldehyde, propionic acid, and others.

Incidentally, since acetaldehyde is separated by the aftermentioned acetaldehyde separation step, the concentration of acetaldehyde in the reactor is held down and is relatively low in spite of the continuous reaction. For example, the concentration of acetaldehyde in the reactor (or reaction system) may be not more than 1000 ppm (e.g., 0 or detection limit to 700 ppm) and preferably not more than 400 ppm (e.g., 5 to 300 ppm) in the liquid phase in the reactor in the process operation.

Moreover, inside of the reactor, by-products derived from acetaldehyde is also produced (for example, crotonaldehyde, which is a reducing substance, produced by aldol condensation of acetaldehyde; 2-ethylcrotonaldehyde produced by aldol condensation of hydrogenated crotonaldehyde and acetaldehyde; and hexyl iodide produced through aldol condensation of three acetaldehyde molecules, hydrogenation, and iodization). According to the present invention, since the fluctuation of the concentration of acetaldehyde in the reactor is also inhibited, the combination of such inhibition and the low acetaldehyde concentration mentioned above can significantly decrease the formation of by-products derived from acetaldehyde. That is, these by-products are often produced in proportion to the second to third power of the acetaldehyde concentration, and the inhibited (or decreased) acetaldehyde concentration and fluctuation can efficiently induce inhibition of the production of by-product.

The space time yield of the objective carboxylic acid (acetic acid) in the reaction system may be, for example, about 5 mol/Lh to 50 mol/Lh, preferably about 8 mol/Lh to 40 mol/Lh, and more preferably about 10 mol/Lh to 30 mol/Lh.

The vapor component may be withdrawn from the top of the reactor for the purpose of the pressure control of the reactor or others, and the withdrawn vapor component may be cooled with a condenser, a heat exchanger or other means to remove part of the reaction heat. The cooled vapor component may be separated into a liquid component (containing acetic acid, methyl acetate, methyl iodide, acetaldehyde, water, and others) and a gaseous component (containing carbon monoxide, hydrogen, and others), and the liquid component may be recycled to the reactor.

(Flash Evaporation Step)

In the flash distillation step (flasher), from the reaction mixture fed from the reaction step or the reactor to the flasher (evaporator or flash distillation column), a higher boiling point component (2B) containing at least a higher boiling point catalyst component (a metal catalyst component, e.g., a rhodium catalyst and a halide salt) is separated as a liquid (component), and a lower boiling point component (2A) containing acetic acid and methyl iodide is separated as a vapor (component).

As described above, the feed amount of the reaction mixture to the flasher fluctuates. With respect to the degree of the fluctuation, assuming that the average flow rate (in terms of liquid volume; the same applies in others unless otherwise noted) of the reaction mixture to be fed to the flasher is 100, the flow rate of the reaction mixture to be fed to the flasher is about 90 to 110 (e.g., about 93 to 107), preferably about 95 to 105 (e.g., about 97 to 103), and more preferably about 98 to 102 (e.g., about 98.5 to 101.5) in the process operation.

The separation (flash distillation) of the metal catalyst component may be conducted by a conventional separation method or a conventional separation apparatus, and may usually be carried out with the use of a flash distillation column. Moreover, the metal catalyst component may be separated by means of flash distillation in combination with a mist-collecting method or a solid-collecting method which is widely used in industrial application.

In the flash evaporation step, the reaction mixture may be separated into the vapor component (or vaporized stream) and the liquid component (or liquid stream) with or without heating. For example, in adiabatic flash, the reaction mixture may be separated into the vapor component and the liquid component without heating and with reduced pressure; in thermostatic flash, the reaction mixture may be separated into the vapor component and the liquid component with heating (and reduced pressure). The reaction mixture may be separated into the vapor component and the liquid component by combining these flash conditions. These flash distillation steps may be carried out, for example, at a temperature of about 80 to 200° C. under a pressure (absolute pressure) of about 50 to 1,000 kPa (e.g., about 100 to 1,000 kPa), preferably about 100 to 500 kPa, and more preferably about 100 to 300 kPa.

The separation step of the catalyst may be composed of a single step, or may be composed of a plurality of steps in combination. The higher boiling point catalyst component (metal catalyst component) separated by such step(s) may usually be recycled to the reaction system, as shown in the embodiment of the figure.

Moreover, part of the lower boiling point component (2A) may be recycled to the reactor or the reaction system, as described above. The lower boiling point component (2A) to be recycled may be heat-removed and condensed in a suitable method (e.g., a method using a heat exchanger or a condenser) to be recycled to the reactor. The proportion of the lower boiling point component (2A) to be recycled may for example be about 1 to 50% by volume (e.g., about 5 to 45% by volume), preferably about 10 to 40% by volume, and more preferably about 10 to 30% by volume.

The separated lower boiling point component (2A) contains product acetic acid, in addition, hydrogen iodide, a co-catalyst (such as methyl iodide), methyl acetate, water, by-product (s) (e.g., an aldehyde such as acetaldehyde, and propionic acid) and others, and is fed to a distillation column for collecting acetic acid. The proportion of the lower boiling point component (2A) to be fed to the acetic acid collection step in the whole reaction mixture may for example be about 5 to 50% by weight, preferably about 8 to 40% by weight, and more preferably about 10 to 35% by weight (e.g., about 12 to 30% by weight).

(Acetic Acid Collection Step)

In the acetic acid collection step, the lower boiling point component (2A) is fed to the distillation column (splitter column) and separated into a lower boiling point component (3A) containing methyl iodide and by-product acetaldehyde and a stream (3B) containing acetic acid to collect acetic acid. Specifically, in the distillation column, the lower boiling point component (3A) (overhead) containing methyl iodide, methyl acetate, acetaldehyde, water, and others is separated as a vapor from the lower boiling point component (2A)

(acetic acid stream) fed from the flasher; and the liquid stream (3B) (side cut stream, side stream) containing acetic acid is withdrawn by side cut. Incidentally, in the distillation column, a higher boiling point component (3C) containing acetic acid, water, propionic acid, an entrained metal catalyst component, the halide salt, and others may be separated. The higher boiling point component (3C) may be removed (discharged) from the bottom of the distillation column. Since the higher boiling point component (3C) contains a useful component such as the metal catalyst component or acetic acid remaining without being evaporated, the component (3C) may be recycled to the reactor (or reaction step), the flash evaporation step (or distillation column), or others, as the embodiment of the figure. Incidentally, prior to recycling, propionic acid, which deteriorates the quality of acetic acid as a final product, may be removed off. The acetic acid stream (crude acetic acid solution) is usually dehydrated in the next distillation column and then introduced into an acetic acid purification column for separating higher and lower boiling point components by distillation to give product acetic acid.

Moreover, as described later, the higher boiling point component (3C) to be recycled may be recycled to the reaction system or others through a storage vessel having a buffering function.

As described above, the amount of the lower boiling point component (2A) to be fed to the distillation column is also affected by the fluctuation of the amount fed from the reactor and fluctuates. With respect to the degree of the fluctuation, for example, assuming that the average flow rate of the lower boiling point component (2A) to be fed to the distillation column is 100, the flow rate of the lower boiling point component (2A) to be fed to the distillation column (2A) is about 90 to 110 (e.g., about 93 to 107), preferably about 95 to 105 (e.g., about 97 to 103), and more preferably about 98 to 102 (e.g., about 98.5 to 101.5) in the process operation.

In the distillation column (splitter column), the position of a feed port for feeding the lower boiling point component (2A) is not particularly limited to a specific one. For example, the position of the feed port may be in an upper part, a middle part, or a lower part of the distillation column. Moreover, in the distillation column, the lower boiling point component (2A) may be fed at an upper position or a lower position relative to a side stream port for side-cutting the acetic acid stream. Further, the position of the side stream port for side-cutting the acetic acid stream may be in an upper part, a middle part, or a lower part of the distillation column, and usually, the position of the side stream port is preferably in a middle part or a lower part of the distillation column.

As the distillation column, there may be used a conventional distillation column, for example, a plate column, a packed column, and a flash distillation column. A distillation column such as a plate column or a packed column may be usually employed. Incidentally, the material of (or for forming) the distillation column is not limited to a specific one, and a glass, a metal, a ceramic, or others can be used. In usual, a distillation column made of a metal is used practically.

The distillation temperature and pressure in the distillation column may suitably be selected depending on the condition such as the species of the distillation column, or the main subject (target) for removal selected from the lower boiling point component and the higher boiling point component. For example, in the distillation column, the inner temperature of the column (usually, the temperature of the column top) may be adjusted by adjusting the inner pressure of the column, and may be, for example, about 20 to 180° C., preferably about 50 to 150° C., and more preferably about 100 to 140° C.

Moreover, for the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde highly (or with a high precision) in the distillation column, the theoretical number of plates may be about 10 to 80, preferably about 20 to 60, and more preferably about 25 to 50. Further, in the distillation column, the reflux ratio may be selected from, for example, about 0.5 to 3,000, and preferably about 0.8 to 2,000 depending on the above-mentioned theoretical number of plates, or may be reduced by increasing the theoretical number of plates.

The separated lower boiling point component (3A) practically contains methyl iodide, acetaldehyde, and in addition methyl acetate, water, acetic acid, and others. The proportion of the lower boiling point component (3A) to be fed to the condensation step or decanter may for example be about 5 to 70% by volume, preferably about 10 to 65% by volume, and more preferably about 12 to 60% by volume (e.g., about 15 to 50% by volume) in the total lower boiling point component (2A).

(Condensation and Discharge Step)

In the condensation and discharge step (which may simply be referred to as the condensation step), the separated lower boiling point component (or condensate) (3A) is temporarily held (or stored) in the decanter (or storage vessel) while condensing, and then discharged to be subjected to at least the acetaldehyde separation step. Moreover, according to the present invention, the amount of the lower boiling point component (3A) to be held (or the amount of the lower boiling point component (3A) to be discharged) in condensation and discharge step is regulated (or controlled) in the process operation based on the flow rate fluctuation of the lower boiling point component (3A) to be fed to the decanter.

That is, as described above, the amount of the lower boiling point component (3A) to be fed to the decanter widely fluctuates through a series of steps. For example, the fluctuation is large as follows: assuming that the average flow rate of the lower boiling point component (or condensate) (3A) to be fed to the decanter is 100, the flow rate of the lower boiling point component (or condensate) (3A) to be fed to the decanter is about 80 to 120 (e.g., about 85 to 115), preferably about 90 to 110 (e.g., about 93 to 107), and more preferably about 95 to 105, in the process operation. According to the present invention, in order to ease the flow rate fluctuation, the amount of the lower boiling point component (3A) to be held in the decanter is adjusted.

Concrete examples of the method for adjusting (or controlling) the amount of the lower boiling point component (3A) to be held may include (1) a method in which the lower boiling point component (3A) is discharged so that the fluctuation of the amount or liquid level of the lower boiling point component (3A) to be held in the decanter may be reduced (e.g., a method shown in FIG. 1) and (2) a method in which a decanter having a buffering function is used as the decanter to ease the fluctuation of the feed amount of the lower boiling point component (3A) in the decanter (e.g., a method shown in FIG. 2). These methods may be combined.

According to the method (1), the discharge amount of the lower boiling point component (3A) is adjusted so as to correspond to the fluctuation of the lower boiling point component (3A) to be fed to the decanter. In this method, for example, assuming that the average liquid level of the lower boiling point component (3A) to be held to the decanter is 100, the liquid level of the lower boiling point component (3A) to be held to the decanter may be adjusted to about 80 to 120 (e.g., about 85 to 115), preferably about 90 to 110 (e.g., about 93 to 107), and more preferably about 95 to 105 (e.g., about 98 to 102) in the process operation (or the discharge amount of the lower boiling point component (3A) may be adjusted). Moreover, in the case where the lower boiling point component (3A) to be held to the decanter is phase-separated (or is separated into two layers (or two phases)), assuming that the average interface level is 100, the interface level of the lower boiling point component (3A) to be held to the decanter (for example, the liquid level of the lower layer) may be adjusted to about 80 to 120 (e.g., about 85 to 115), preferably about 90 to 110 (e.g., about 93 to 107), and more preferably about 95 to 105 (e.g., about 98 to 102) in the process operation (or the discharge amount of the lower boiling point component (3A) may be adjusted).

Moreover, according to the method (1), assuming that the average amount of the lower boiling point component (3A) to be held to the decanter is 100 on the basis of liquid volume, the amount of the lower boiling point component (3A) to be held to the decanter may be adjusted to constant or almost or substantially constant [for example, about 80 to 120 (e.g., about 85 to 115), preferably about 90 to 110 (e.g., about 93 to 107), and more preferably about 95 to 105 (e.g., about 98 to 102)] in the process operation.

In the method (1), the liquid level or the like may be adjusted using the above-mentioned sensor (liquid level sensor) or other means or may be adjusted by equipping the decanter with a suitable means for discharging the lower boiling point component (3A) when the liquid level reaches a predetermined liquid level.

In the method (2), it is sufficient that the decanter having a buffering function has a capacity enough to ease the feed amount fluctuation of the lower boiling point component (3A). As described above, the decanter can generally be selected based on, as an index, the range enough to keep at the retention time of the lower boiling point component (3A) in the decanter, for example, the retention time (or average retention time) of not less than 1 minute [e.g., not less than 2 minutes (e.g., about 2.5 minutes to 3 hours), preferably not less than 3 minutes [e.g., not less than 4 minutes (e.g., about 5 to 60 minutes)], more preferably not less than 6 minutes (e.g., about 8 to 50 minutes), and particularly not less than 12 minutes (e.g., about 15 to 40 minutes)]. Even when the feed amount of the lower boiling point component (3A) fluctuates, use of the decanter ensuring the sufficient retention time can ease the fluctuation inside the decanter, which enables the stable operation of the process. As described later, in the case where the lower boiling point component (3A) is separated into an upper layer and a lower layer, it is sufficient that the retention time of the whole layer is in the above-mentioned range. Moreover, the retention time of the upper layer is not necessarily needed to be the same as the retention time of the lower layer. The retention time of one of these layers may be lengthened (or shortened).

In the method (1), the retention time of the lower boiling point component (3A) in the decanter is not particularly limited to a specific one, and may for example be not less than 5 seconds (e.g., not less than 10 seconds), preferably not less than 15 seconds (e.g., not less than 20 seconds), and more preferably not less than 30 seconds. Moreover, in the method (1), a decanter having a buffering function available for the method (2) may be used to keep at the sufficient retention time.

The lower boiling point component (3A) is sometimes separated into the upper layer and the lower layer in the decanter, as described above. In this case, the lower boiling point component (3A) may be discharged from either the upper layer or the lower layer or both upper and lower layers. In the lower boiling point component (3A) to be fed to the decanter, the volume ratio of the upper layer relative to the lower layer may be selected from the range of about 0.2/1 to 5/1 (e.g., about 0.3/1 to 3/1) as a ratio of the former/the latter, and for example be about 0.5/1 to 1.5/1, preferably about 0.6/1 to 1.4/1, and more preferably about 0.7/1 to 1.3/1 as a ratio of the former/the latter. In the upper layer and the lower layer, the feed amount fluctuation is in the same range as described above. Moreover, in the method (1), when the lower boiling point component (3A) is separated into the upper layer and the lower layer, it is sufficient to reduce the fluctuation of the liquid level (or the holding amount) as a whole so as to fall within the above-mentioned range. The fluctuation of the liquid level (or the holding amount) of each of both layers may be reduced so as to fall within the above-mentioned range. For example, as the embodiment of FIG. 1 described above, the liquid level fluctuation of both the upper layer and the lower layer can be reduced by changing the flow rate of the lower boiling point component (3A) to be discharged from each of the upper layer and the lower layer in response to the flow rate fluctuation of the lower boiling point component (3A) to be fed to the decanter.

The lower boiling point component (3A) discharged from the decanter is fed to the acetaldehyde separation step (or acetaldehyde distillation column). When the lower boiling point component (3A) is directly fed without adjustment of the flow rate, stabilized acetaldehyde separation is sometimes inhibited under the influence of the fluctuation of the amount of the lower boiling point component (3A) to be fed to the decanter. Thus, according to the present invention, the amount of the lower boiling point component (3A) to be fed to the separation and recycling step in addition to the amount of the lower boiling point component (3A) to be held to the decanter may be adjusted.

Specifically, assuming that the average flow rate of the lower boiling point component (3A) to be fed to the separation and recycling step is 100, the flow rate of the lower boiling point component (3A) to be fed to the separation and recycling step may be adjusted (that is, substantially be stabilized) so as to be constant or almost constant [for example, about 90 to 110 (e.g., about 93 to 107), preferably about 95 to 105 (e.g., about 97 to 103), more preferably about 98 to 102, and particularly about 98.5 to 101.5] in the process operation.

The method for adjusting or controlling the amount of the lower boiling point component (3A) to be fed to the separation and recycling step may include, for example, (a) a method for circulating part of the lower boiling point component (3A) discharged from the decanter to a step different from the separation and recycling step (particularly, at least the reactor or reaction step) (e.g., the embodiment shown in FIG. 1), (b) a method for feeding the separation and recycling step with the lower boiling point component (3A) discharged from the decanter through a storage vessel having a buffering function (e.g., the embodiment shown in FIG. 1), and (c) a method for adjusting the amount of the lower boiling point component (3A) to be discharged from the decanter to keep constant (or almost constant) (e.g., the embodiment shown in FIG. 2). These methods may be combined.

For the method (a), part of the discharged lower boiling point component (3A) is circulated (recycled) in response to the fluctuation of the lower boiling point component (3A) to be fed to the decanter without subjecting to the separation and recycling step, and thus the amount of the lower boiling point component (3A) to be fed to the separation and recycling step can be adjusted so as to be constant or almost constant. Specifically, in the case where the amount of the lower boiling point component (3A) to be discharged from the decanter fluctuates, the fluctuation of the lower boiling point component (3A) to be fed to the separation and recycling step can be reduced at a high level by changing the amount of the lower boiling point component (3A) to be circulated. The step (or apparatus) for recycling the lower boiling point component (3A) is not particularly limited to a specific one as far as the step (or apparatus) is not a separation and recycling step (or acetaldehyde separation column). The step (or apparatus) for recycling the lower boiling point component (3A) may be the reactor (or reaction step), the acetic acid collection step (or distillation column), or others. The lower boiling point component (3A) may be recycled to a plurality of steps. In particular, the lower boiling point component (3A) may be recycled to at least the reaction step.

In the method (a), the amount to be circulated may be selected depending on the throughput of the acetaldehyde separation column, the degree of the fluctuation of the lower boiling point component (3A), or others. For example, the amount to be circulated may be not less than 2% (e.g., about 3 to 99%), preferably not less than 5% (e.g., about 7 to 95%), more preferably not less than 10% (e.g., about 12 to 90%), and particularly not less than 20% (e.g., about 20 to 90%) of the average flow rate of the lower boiling point component (3A) to be fed to the decanter. In particular, the circulation of a relatively large amount [for example, not less than 40% (e.g., about 40 to 90%), preferably about 50 to 90% (e.g., about 55 to 85%), more preferably about 60 to 80%, and usually about 55 to 90% (e.g., about 65 to 85%) of the average flow rate of the lower boiling point component (3A) to be fed to the decanter] of the lower boiling point component (3A) efficiently achieves both stable operation of the process and removal of acetaldehyde.

The proportion of the lower boiling point component (3A) (or the average flow rate of the lower boiling point component (3A)) to be circulated to the reaction system (or reaction step or reactor) in the total lower boiling point component (3A) to be circulated may be about 5 to 100% by volume, preferably about 10 to 90% by volume, more preferably about 15 to 80% by volume, and particularly about 20 to 75% by volume (for example, about 25 to 70% by volume). Moreover, in the case where the lower boiling point component (3A) is circulated to the reactor and the acetic acid collection step (or distillation column), the ratio (volume ratio) of the component (3A) to be circulated to the reactor relative to that to be circulated to the acetic acid collection step may be about 95/5 to 5/95 (e.g., about 90/10 to 10/90), preferably about 85/15 to 15/85 (e.g., about 80/20 to 20/80), more preferably about 75/25 to 25/75 (e.g., about 70/30 to 30/70), and particularly about 65/35 to 35/65 (e.g., about 60/40 to 40/60) as a ratio of the former/the latter. Further, the ratio (volume ratio) of the lower boiling point component (3A) (or the average flow rate thereof) to be circulated to the reactor relative to the lower boiling point component (3A) (or the average flow rate thereof) to be fed to the separation and recycling step may be about 95/5 to 10/90 (e.g., about 90/10 to 15/85), preferably about 85/15 to 20/80 (e.g., about 80/20 to 25/75), more preferably about 75/25 to 35/65 (e.g., about 70/30 to 40/60), and particularly about 70/30 to 45/55 (e.g., about 65/35 to 50/50) as a ratio of the former/the latter.

In the case where the lower boiling point component (3A) is separated into an upper layer and a lower layer inside the decanter, either the upper layer (part of all of the upper layer) or the lower layer (part of all of the lower layer) may be recycled. In particular, the both layers may be recycled to the reaction system. When the both layers are recycled, the volume ratio of the lower boiling point component (3A) of the upper layer to be recycled relative to the lower boiling point component (3A) of the lower layer to be recycled may be about 99/1 to 1/99, preferably about 95/5 to 5/95, and more preferably about 90/10 to 10/90 as a ratio of the former/the latter. Moreover, for recycling of part of the upper layer, the proportion of the lower boiling point component (3A) to be recycled in the total lower boiling point component (3A) of the upper layer may be, for example, about 3 to 90% by volume, preferably about 5 to 80% by volume (e.g., about 10 to 75% by volume), and more preferably about 15 to 65% by volume (e.g., about 20 to 60% by volume). Further, for recycling of part of the lower layer, the proportion of the lower boiling point component (3A) to be recycled in the total lower boiling point component (3A) of the lower layer may be, for example, about 5 to 95% by volume, preferably about 10 to 90% by volume (e.g., about 15 to 85% by volume), and more preferably 20 to 80% by volume (e.g., about 25 to 75% by volume).

If necessary, the lower boiling point component (3A) to be circulated to the reaction system or others may be subjected to a conventional method (for example, the after-mentioned extraction) for separation of acetaldehyde and then circulated to the reaction system or others.

For the method (b), before the lower boiling point component (3A) discharged from the decanter is fed to the separation and recycling step, the lower boiling point component (3A) is retained in a storage vessel (such as a buffer tank) having a buffering function. The temporal retention of lower boiling point component (3A) in the storage vessel further eases the flow rate fluctuation in the storage vessel and allows the lower boiling point component (3A) to be fed to the separation and recycling step at a constant or almost constant flow rate, and thus the stable operation of the process is achievable.

The storage vessel having a buffering function can be selected based on the degree of the flow rate fluctuation or others, as the same as described above, or may be selected according to the retention time of the lower boiling point component (3A). In the storage vessel, the retention time of the lower boiling point component (3A) is not particularly limited to a specific one, and may for example be not less than 0.5 minutes [for example, not less than 1 minute (e.g., about 1.5 minutes to 3 hours)], preferably not less than 2 minutes [for example, not less than 3 minutes (e.g., about 4 to 60 minutes)], more preferably not less than 6 minutes (e.g., about 8 to 50 minutes), and particularly not less than 12 minutes (e.g., about 15 to 40 minutes).

When the flow rate fluctuation of the lower boiling point component (3A) can be eased in the decanter in some degree, the retention time of the lower boiling point component (3A) in the storage vessel can also be shortened. Thus, the retention time of the lower boiling point component (3A) in the storage vessel may be determined in connection with the retention time of the lower boiling point component (3A) in the decanter. For example, the storage vessel may be selected so that the total time of the retention time of the lower boiling point component (3A) in the decanter and the retention time of the lower boiling point component (3A) in the storage vessel may ne not less than 1 minute [for example, not less than 1.5 minutes (e.g., about 2 minutes to 3 hours)], preferably not less than 3 minutes [for example, not less than 4 minutes (e.g., about 5 to 60 minutes)], more preferably not less than 6 minutes (e.g., about 8 to 50 minutes), and particularly not less than 12 minutes (e.g., about 15 to 40 minutes).

It is sufficient that the storage vessel having a buffering function is provided (or installed) in a step prior to the separation and recycling step. The storage vessel may be provided (or installed) in a bottom of the after-mentioned acetaldehyde separation column.

For the method (c), the amount of the lower boiling point component (3A) to be discharged from the decanter is kept constant (or almost constant) in itself [for example, assuming that the average flow rate of the lower boiling point component (3A) to be discharged from the decanter is 100, the amount of the lower boiling point component (3A) to be discharged from the decanter in the process operation is regulated to about 90 to 100 (e.g., about 95 to 105), preferably about 98 to 102, and more preferably about 98.5 to 101.5]. Since the amount of the lower boiling point component (3A) to be discharged from the decanter is substantially kept constant, the method (c) may preferably be combined with a method for easing the flow rate fluctuation inside the decanter (for example, the method (2)) in order to operate the process stably.

The position (the position of an outlet) for discharging the lower boiling point component (3A) from the decanter is not particularly limited to a specific one. The position of the outlet may be in an upper part, a middle part, a lower part or a bottom part of the decanter. A plurality of these parts may be combined to provide a plurality of outlets. Moreover, in the case where the lower boiling point component (3A) is separated into an upper layer and a lower layer inside the decanter, the lower boiling point component (3A) may be discharged from a position corresponding to the upper layer, a position corresponding to the lower layer, or both.

(Separation and Recycling Step)

In the separation and recycling step, the lower boiling point component (3A) discharged or fed in a condensed state (liquid state) by the condensation step is separated into acetaldehyde and a liquid residue (or residual liquid), and the liquid residue is recycled to a step from the reaction system to the acetaldehyde separation.

The discharged lower boiling point component (3A) may further contain a vapor component withdrawn from the top of the reactor, a higher boiling point component (3C), or others. The lower boiling point component (3A) to be subjected to separation contains acetaldehyde, methyl iodide, and in addition, methyl acetate, water, other carbonyl impurities (e.g., crotonaldehyde and butyraldehyde) in many cases. In the lower boiling point component (3A), the proportion of acetaldehyde may be about 0.05 to 50% by weight, the proportion of methyl iodide may be about 0.5 to 90% by weight, the proportion of methyl acetate may be about 0 to 15% by weight, the proportion of acetic acid may be about 0 to 80% by weight, and the proportion of water may be about 0.1 to 40% by weight.

The method for separating acetaldehyde is not particularly limited to a specific one as far as the liquid residue can be obtained. As the separation method, a conventional method [for example, extraction, distillation (e.g., separation and distillation of a process liquid containing acetaldehyde using one or a plurality of distillation columns), a combination thereof, and extractive distillation] may be used.

Representatively, a preferably usable method includes a method which comprises feeding the lower boiling point component (3A) to the distillation column (acetaldehyde separation column) and separating the lower boiling point component (3A) by distillation into a lower boiling point component (4A) containing acetaldehyde and a liquid residue (bottom fraction or column bottom fraction). The production of paraldehyde and/or metaldehyde may be decreased by feeding water to the distillation column and increasing the pressure or/and the distillation temperature. Further, paraldehyde and metaldehyde may be positively produced by modifying the distillation conditions so that acetaldehyde can be separated and removed in the form of paraldehyde or metaldehyde from the bottom of the distillation column. In this case, clogging due to crystallization of metaldehyde may be reduced by adding a solvent for dissolving metaldehyde (e.g., methanol) to the column.

The liquid residue, which is the residue after separation of acetaldehyde by distillation, is usually separated as a liquid residue (higher boiling point component (4B)) containing methyl iodide which is a useful component and is recycled. Prior to the separation of acetaldehyde, an off gas component may be removed beforehand by using a condenser, a cooler, or others.

As the acetaldehyde separation column, a conventional distillation column, for example, a plate column, a packed column, and a flash distillation column, may be used. A distillation column such as a plate column or a packed column may usually be employed.

The temperature (the temperature of the column top) and the pressure (the pressure of the column top) in the acetaldehyde separation column may be selected depending on the boiling point of acetaldehyde and that of methyl iodide as well as the types of the distillation column and others, and is not particularly limited to a specific one as far as the lower boiling point component (4A) containing at least acetaldehyde is separable from the lower boiling point component (3A) by utilizing difference between acetaldehyde and other components (particularly methyl iodide) in boiling point. For example, for the plate column, the column top pressure is about 10 to 1000 kPa, preferably about 10 to 700 kPa, and more preferably about 100 to 500 kPa in terms of absolute pressure. The inner temperature of the column (the column top temperature) is, for example, about 10 to 80° C., preferably about 20 to 70° C., and more preferably about 40 to 60° C. The number (theoretical number) of plates of the distillation column may for example be about 5 to 80, preferably about 8 to 60, and more preferably about 10 to 50.

In the acetaldehyde separation column, the reflux ratio may be selected from about 1 to 1000, preferably about 10 to 800, and more preferably about 50 to 600 (e.g., about 100 to 600) depending on the above-mentioned theoretical number of plates.

The recycling of the liquid residue (or higher boiling point component (4B)) is not particularly limited to a specific step as far as the recycling step is placed from the reaction system to the acetaldehyde separation. The step may be any of the reaction step (or reactor), the flash distillation step (or flash distillation column), and the acetic acid collection step (or distillation column). As in the embodiment of the figure, the higher boiling point component (4B) may be recycled to the acetaldehyde distillation column, or may be recycled to a combination of these steps. The liquid residue (or higher boiling point component (4B)) after acetaldehyde separation is usually recycled to at least the reactor.

The liquid residue (or higher boiling point component (4B)) may be recycled directly or recycled through a storage vessel having a buffering function (e.g., a buffer tank). Use of the storage vessel having a buffering function eases the flow rate fluctuation in the storage vessel and allows easy recycling of the liquid residue at a constant or almost constant flow rate, even if the flow rate of the liquid residue fluctuates. Thus the storage vessel can reduce the influence of the flow rate fluctuation on the recycling step.

With respect to the flow rate fluctuation of the liquid residue (higher boiling point component (4B)), for example, assuming that the average flow rate of the liquid residue is 100, the flow rate of the liquid residue may be about 85 to 115 (e.g., about 90 to 110), preferably about 93 to 107 (e.g., about 94 to 106), and more preferably about 95 to 105 in the process operation.

The storage vessel having a buffering function may be selected based on the degree of the flow rate fluctuation, in the same manner as in the condensation step, and may be selected based on the desired retention time of the liquid residue. In the storage vessel, the retention time of the liquid residue is not particularly limited to a specific one, and may for example be not less than 1 minutes (e.g., about 2 minutes to 3 hours), preferably not less than 3 minutes (e.g., about 4 to 60 minutes), and more preferably not less than 12 minutes (e.g., about 15 to 40 minutes).

When the liquid residue is recycled through the storage vessel having a buffering function, the fluctuation of the flow rate of the liquid residue (higher boiling point component (4B)) can be decreased. For example, assuming that the average flow rate of the liquid residue is 100, the flow rate of the liquid residue may be about 90 to 110 (e.g., about 93 to 107), preferably about 95 to 105, and more preferably about 96 to 104 (e.g., about 97 to 103) in the process operation.

For recycling the liquid residue (higher boiling point component (4B)) to the acetaldehyde separation column, in order to reduce the flow rate fluctuation in the separation column at a high level, the flow rate of the higher boiling point component (4B) to be recycled to the separation column may be constant or almost constant [for example, assuming that the average flow rate of the liquid residue is 100, the flow rate of the liquid residue to be recycled to the separation column may be about 95 to 105, preferably about 97 to 103, and more preferably about 98 to 102 (e.g., about 99 to 101) in the process operation].

The separated lower boiling point component (4A) containing acetaldehyde may be discharged as it is. Since the lower boiling point component (4A) sometimes contains a useful component such as methyl iodide, methyl iodide (or a component containing methyl iodide, for example, a component containing methyl iodide, methyl acetate, and others) may be collected from the lower boiling point component (4A) and recycled.

The method for separating each of acetaldehyde and methyl iodide (or a component containing methyl iodide) from the lower boiling point component (4A) is not particularly limited to a specific one, and may include a conventional method (for example, extraction, distillation). Representative examples of the method may include (i) a method for separating each of methyl iodide and acetaldehyde by distilling the lower boiling point component (4A), (ii) a method for separating each of methyl iodide and acetaldehyde by water extraction, which takes advantage of the miscibility of acetaldehyde with water and the immiscibility of methyl iodide with water. From the viewpoint of the inhibition of production of metaldehyde or others, the water extraction (ii) is preferred. According to the method, since the increase in hydrogen ion concentration in the distillation solution due to ester degradation or others inhibits production of paraldehyde and metaldehyde, acetaldehyde can efficiently be condensed to a high level and removed.

The extraction temperature and the extraction time are not particularly limited to specific ones. For example, the extraction may be carried out at a temperature of 0° C. to 100° C. for about 1 second to 1 hour. The extraction pressure is not particularly limited to a specific one, and an advantageous condition can be selected based on costs, and others. As the extractor, for example, there may be used a combination of a mixer with a settler, a combination of a static mixer with a decanter, an RDC (rotated disk contactor), a Karr column, a spray column, a packed column, a perforated plate column, a baffled column, a pulse column, and others.

The recycling of methyl iodide (or a component containing methyl iodide) is not particularly limited to a specific step as far as the recycle step is placed from the reaction system to the acetaldehyde separation. Methyl iodide may be recycled to any of the reaction step (or reactor), the flash distillation step (or flash distillation column), and the acetic acid collection step (or distillation column). As the embodiment of the figure, methyl iodide may be recycled (recycled as the higher boiling point component (4B)) to the acetaldehyde-separating column, or may be recycled to a combination of these steps.

EXAMPLES

The following examples are intended to describe this invention in further detail and should by no means be interpreted as defining the scope of the invention.

Example 1

In the apparatus (or process) of FIG. 1, acetic acid production process was carried out continuously as shown in FIG. 1 except that the lower boiling point component (3A) was fed to the acetaldehyde separation column 6 without going through the buffer tank 5. The detail of the process will be described below.

A liquid reaction medium had the following composition (or formulation): methyl iodide (13% by weight), water (8% by weight), methyl acetate (1.3% by weight), acetic acid (73.6% by weight), lithium iodide (5% by weight), and rhodium (800 ppm by weight). The liquid reaction medium was fed to the reactor 1, and the process was started. Throughout the process, the variation in the flow rate of the liquid reaction medium fed from the reactor 1 to the flasher 2 was in the range of about ±1.6% relative to the average flow rate. In the flasher 2, about 27% by weight of the total liquid reaction medium was fed to the splitter column 3 as the lower boiling point component (2A) (the variation in the flow rate was in the range of ±1% relative to the average flow rate); the remaining higher boiling point component (2B) was recycled to the reactor 1 without any treatment. Part (about 19% by volume) of the volatilized lower boiling point component (2A) was fed to the hold tank 9 for removal of heat, and recycled to the reactor 1.

In the splitter column 3, the volatile component (2A) was separated by distillation into the lower boiling point component (3A) (about 50% by volume), the acetic acid-containing stream (3B), and the higher boiling point component (3C). The acetic acid-containing stream (3B) was withdrawn by side cut, and the higher boiling point component (3C) was directly recycled to the reactor. In the splitter column 3, the total amount of a component fed through the line 12 and a component fed through the after-mentioned line 30 was distilled, and the volatilized component was separated as the lower boiling point component (3A).

Meanwhile, when the lower boiling point component (3A) was fed to the decanter 4, the variation in the flow rate was in the range of ±5% relative to the average flow rate (48.5 m³/hour). The lower boiling point component (3A) has the following composition (or formulation): methyl iodide (61% by weight), methyl acetate (6% by weight), acetic acid (6% by weight), water (24% by weight), and acetaldehyde (0.27% by weight).

In the decanter 4, the lowerboilingpoint component (3A) was separated into an upper layer and a lower layer (the former/the latter (volume ratio)=1.1/1). The lower boiling point component (3A) was discharged through the line 17 and the line 18 such that the liquid level and the interface level of the lower boiling point component (3A) to be held in the decanter 4 were maintained substantially constant (such that the fluctuation of the liquid level was about ±1% relative to the average liquid level and the fluctuation of the interface level (or the liquid level of the lower layer) was about ±1% relative to the average interface level). That is, the liquid level and the interface level of the lower boiling point component (3A) in the decanter 4 were maintained substantially constant by changing the flow rate of the lower boiling point component (3A) to be discharged through the line 17 and the line 18 so as to correspond to the flow rate fluctuation of the lower boiling point component (3A) to be fed to the decanter 4 and by adjusting the retention time of the lower boiling point component (3A) in the decanter 4.

The discharged lower boiling point component (3A) was fed to the line 19 (or the line 20) such that the flow rate thereof was substantially constant (the fluctuation of the flow rate was about ±1.5% relative to the average flow rate) by partly recycling the lower boiling point component (3A) through the line 17a and the line 18a, and fed to the distillation column 6 without any treatment. The flow rate of the lower boiling point component (3A) to be fed to the line 19 was adjusted by changing the amount of the lower boiling point component (3A) to be circulated to the reaction system (reactor) through the line 17a and the line 18a and by adjusting the retention time of the lower boiling point component (3A) in the decanter 4. In the decanter 4, the retention time of the upper layer was 13 minutes and the retention time of the lower layer was 6 minutes. That is, the amount of the lower boiling point component (3A) to be fed to each of the line 17b and the line 18b was successfully maintained substantially constant by changing the flow rate of each of the line 17a and the line 18a so as to correspond to the flow rate fluctuation of the lower boiling point component (3A) to be discharged from the decanter 4. For example, the variation in the flow rate of the lower boiling point component (3A) to be fed to the line 18a was in the range of about ±10%. Thus, the flow rate of the lower boiling point component (3A) to be fed to the line 19 (further the flow rate of the lower boiling point component (3A) to be fed to the distillation column 6) was successfully maintained substantially constant.

With respect to the lower boiling point component (3A) of the upper layer, the proportion of the lower boiling point component (3A) fed to the line 19 (or the line 17b) was 13.5% by volume (corresponding to 25% by volume of the whole upper layer) in the total lower boiling point component (3A) fed to the decanter 4; with respect to the lower boiling point component (3A) of the lower layer, the proportion of the lower boiling point component (3A) fed to the line 19 (or the line 18b) was 13.5% by volume (corresponding to 28% by volume of the whole lower layer) in the total lower boiling point component (3A) fed to the decanter 4.

That is, 27% by volume of the total lower boiling point component (3A) fed to the decanter 4 was fed to the line 19 (or the distillation column 6), and 73% by volume of the total lower boiling point component (3A) fed to the decanter 4 was recycled. The breakdown of the recycle was as follows: 34% by volume [0% by volume from the upper layer, 34% by volume from the lower layer (corresponding to 72% by volume of the whole lower layer)] of the total lower boiling point component (3A) fed to the decanter 4 was recycled to the reactor 1, and 39% by volume (corresponding to 75% by volume of the whole upper layer) of the total lower boiling point component (3A) fed to the decanter 4 was recycled to the splitter column 3.

The composition of the lower boiling point component (3A) to be fed to the distillation column 6 was as follows: methyl iodide (46% by weight), methyl acetate (6% by weight), acetic acid (10% by weight), water (37% by weight), acetaldehyde (0.3% by weight), and hydrogen iodide (0.01% by weight).

In the distillation column 6 (a distillation column having 80 plates, reflux ratio: 170, feeding plate: the 70th plate from the top, column top temperature: 54° C., column bottom temperature: 82° C.), 0.3% by volume of the lower boiling point component (3A) was withdrawn as the lower boiling point component (4A) from the column top, and the whole amount of the residue was recycled as the higher boiling point component (4B) to the reactor 1 from the column bottom without going through the buffer tank 7. The composition of the lower boiling point component (4A) withdrawn from the column top was as follows: methyl iodide (42% by weight), water (2% by weight), and acetaldehyde (56% by weight).

Moreover, the lower boiling point component (4A) withdrawn from the column top was subjected to water extraction in the extractor 8, so that acetaldehyde was removed, and a raffinate containing methyl iodide was separated. Then the raffinate was divided into two fractions; one fraction was directly recycled to the bottom (10th plate) of the distillation column 6 and the other was directly recycled to the reactor 1. The amount to be recycled to the distillation column 6 was set to constant. The acetaldehyde extraction rate of the lower boiling point component (4A) was 98%. Acetaldehyde (19 kg/hr) was successfully removed by treating the whole liquid (34 kg/hr) withdrawn from the column top of the above-mentioned distillation column having 80 plates. In this way, 59% of the acetaldehyde (32 kg/hr) produced in the reactor was successfully removed.

The above-mentioned process was carried out continuously, and the process was successfully operated stably. After the operation was carried out for a predetermined time (200 hours), the acetaldehyde concentration measured in the reactor was 390 ppm. This revealed that both the stable operation and the removal of acetaldehyde at a high level were achieved successfully. It was found that the resulting product acetic acid had a permanganate time of 240 minutes.

Example 2

Example 2 was conducted in the same manner as in Example 1 except that part of the lower boiling point component (3A) discharged from the decanter 4 was recycled and that the rest was fed to the distillation column 6 in the process as described later.

With respect to the lower boiling point component (3A) of the upper layer, the proportion of the lower boiling point component (3A) fed to the line 19 (or the line 17b) was 0% by volume in the total lower boiling point component (3A) fed to the decanter 4 (that is, the lower boiling point component (3A) of the upper layer is wholly recycled without being fed to the line 19 or the line 17b); with respect to the lower boiling point component (3A) of the lower layer, the proportion of the lower boiling point component (3A) fed to the line 19 (or the line 18b) was 27% by volume (corresponding to 57% by volume of the whole lower layer) in the total lower boiling point component (3A) fed to the decanter 4.

That is, 27% by volume of the total lower boiling point component (3A) fed to the decanter 4 was fed to the line 19 (or the distillation column 6), and 73% by volume of the total lower boiling point component (3A) fed to the decanter 4 was recycled. The breakdown of the recycle was as follows: 34% by volume [13% by volume from the upper layer (corresponding to 25% by volume of the whole upper layer), 21% by volume from the lower layer (corresponding to 43% by volume of the whole lower layer)] of the total lower boiling point component (3A) fed to the decanter 4 was recycled to the reactor 1, and 39% by volume (corresponding to 75% by volume of the whole upper layer) of the total lower boiling point component (3A) fed to the decanter 4 was recycled to the splitter column 3.

According to the above-mentioned step, the discharged lower boiling point component (3A) was fed to the line 19 (or the line 20) such that the flow rate thereof was substantially constant (the fluctuation of the flow rate was about ±2.5% relative to the average flow rate) by partly recycling the lower boiling point component (3A) through the line 18a, and fed to the distillation column 6 without any treatment. The flow rate of the lower boiling point component (3A) to be fed to the line 19 was adjusted by changing the amount of the lower boiling point component (3A) to be circulated to the reaction system (reactor) through the line 18a. That is, the amount of the lower boiling point component (3A) to be fed to the line 18b was successfully maintained substantially constant by changing the flow rate of the line 18a so as to correspond to the flow rate fluctuation of the lower boiling point component (3A) to be discharged from the decanter 4 (the variation in the flow rate of the lower boiling point component (3A) to be fed to the line 18a was in the range of about ±17%). Thus, the flow rate of the lower boiling point component (3A) to be fed to the line 19 (further the flow rate of the lower boiling point component (3A) to be fed to the distillation column 6) was successfully maintained substantially constant.

The composition of the lower boiling point component (3A) to be fed to the distillation column 6 was as follows: methyl iodide (91% by weight), methyl acetate (7% by weight), acetic acid (1% by weight), water (0.3% by weight), acetaldehyde (0.1% by weight), and hydrogen iodide (0.001% by weight).

In the distillation column 6 (a distillation column having 80 plates, reflux ratio: 170, feeding plate: the 70th plate from the top, column top temperature: 54° C., column bottom temperature: 82° C.), 0.3% by volume of the lower boiling point component (3A) was withdrawn as the lower boiling point component (4A) from the column top, and the whole amount of the residue was recycled as the higher boiling point component (4B) to the reactor 1 from the column bottom without going through the buffer tank 7. The composition of the lower boiling point component (4A) withdrawn from the column top was as follows: methyl iodide (43% by weight), water (1% by weight), and acetaldehyde (56% by weight).

Moreover, the lower boiling point component (4A) withdrawn from the column top was subjected to water extraction in the extractor 8, so that acetaldehyde was removed, and a raffinate containing methyl iodide was separated. Then the raffinate was divided into two fractions; one fraction was directly recycled to the bottom (10th plate) of the distillation column 6 and the other was directly recycled to the reactor 1. The amount to be recycled to the distillation column 6 was set to constant. The acetaldehyde extraction rate of the lower boiling point component (4A) was 98%. Acetaldehyde (20 kg/hr) was successfully removed by treating the whole liquid (34 kg/hr) withdrawn from the column top of the above-mentioned distillation column having 80 plates. In this way, 63% of the acetaldehyde (32 kg/hr) produced in the reactor was successfully removed.

The above-mentioned process was carried out continuously, and the process was successfully operated stably. After the operation was carried out for a predetermined time (210 hours), the acetaldehyde concentration measured in the reactor was 375 ppm. This revealed that both the stable operation and the removal of acetaldehyde at a high level were achieved successfully. It was found that the resulting product acetic acid had a permanganate time of 260 minutes.

Example 3

Example 3 was conducted in the same manner as in Example 1 except that part of the lower boiling point component (3A) discharged from the decanter 4 was recycled and that the rest was fed to the distillation column 6 in the process as described later.

In the same manner as in Example 1, the lower boiling point component (3A) was discharged from an upper part of the decanter 4 (a position corresponding to the upper layer) through the line 17 such that the liquid level and the interface level of the lower boiling point component (3A) to be held in the decanter 4 were maintained substantially constant (such that the fluctuation of the liquid level was about ±1% relative to the average liquid level and the fluctuation of the interface level (or the liquid level of the lower layer) was about ±1% relative to the average interface level). That is, the liquid level and the interface level of the lower boiling point component (3A) in the decanter 4 were maintained substantially constant by changing the flow rate of the lower boiling point component (3A) to be discharged through the line 17 along with the flow rate fluctuation of the lower boiling point component (3A) to be fed to the decanter 4.

The flow rate to be fed to the line 19 was successfully relatively reduced by changing the flow rate to be fed to the line 17a (about ±1.5% relative to the average flow rate).

With respect to the lower boiling point component (3A) of the upper layer, the proportion of the lower boiling point component (3A) fed to the line 19 (or the line 17b) was 27% by volume (corresponding to 51% by volume of the whole upper layer) in the total lower boiling point component (3A) fed to the decanter 4; with respect to the lower boiling point component (3A) of the lower layer, the proportion of the lower boiling point component (3A) fed to the line 19 (or the line 18b) was 0% by volume in the total lower boiling point component (3A) fed to the decanter 4 (corresponding to 0% by volume of the whole lower layer, that is, the lower boiling point component (3A) of the lower layer was wholly recycled without being fed to the line 19 or the line 18b).

That is, 27% by volume of the total lower boiling point component (3A) fed to the decanter 4 was fed to the line 19 (or the distillation column 6), and 73% by volume of the total lower boiling point component (3A) fed to the decanter 4 was recycled. The breakdown of the recycle was as follows: 47% by volume [0% by volume from the upper layer, 47% by volume from the lower layer (corresponding to 100% by volume of the whole lower layer)] of the total lower boiling point component (3A) fed to the decanter 4 was recycled to the reactor 1, and 39% by volume (corresponding to 75% by volume of the whole upper layer) of the total lower boiling point component (3A) fed to the decanter 4 was recycled to the splitter column 3.

Then, the discharged lower boiling point component (3A) was fed to the buffer tank 5 and retained at a retention time of 3 minutes to ease the fluctuation of the flow rate in the buffer tank 5, and the lower boiling point component (3A) was fed at a constant flow rate to the distillation column 6.

The composition of the lower boiling point component (3A) to be fed to the distillation column 6 was as follows: methyl iodide (3% by weight), methyl acetate (4% by weight), acetic acid. (19% by weight), water (73% by weight), acetaldehyde (0.5% by weight), and hydrogen iodide (0.01% by weight).

Moreover, the total amount of the higher boiling point component (4B) separated in the distillation column 6 was recycled to the splitter column 3 through the buffer tank 7. Although the variation in the flow rate of the higher boiling point component (4B) separated from the distillation column 6 was about ±4%, the flow rate of the higher boiling point component (4B) to be recycled through the line 23 was successfully maintained substantially constant by recycling the component (4B) through buffer tank 7.

The above-mentioned process was carried out continuously, and the process was successfully operated stably.

Example 4

The acetic acid production process was carried out continuously as shown in the apparatus (or process) of FIG. 1. The conditions including the charging amounts were the same as those of Example 2 except that the process was conducted via buffer tank 5.

In the same manner as in Example 2, the lower boiling point component (3A) was discharged from a lower part of the decanter 4 (a position corresponding to the lower layer) through the line 18 such that the liquid level and the interface level of the lower boiling point component (3A) to be held in the decanter 4 were maintained substantially constant (such that the fluctuation of the liquid level was about ±1% relative to the average liquid level and the fluctuation of the interface level (or the liquid level of the lower layer) was about ±1% relative to the average interface level). That is, the liquid level and the interface level of the lower boiling point component (3A) in the decanter 4 were maintained substantially constant by changing the flow rate of the lower boiling point component (3A) discharged through the line 18 along with the flow rate fluctuation of the lower boiling point component (3A) to be fed to the decanter 4. Then, the discharged lower boiling point component (3A) was fed to the buffer tank 5 and retained at a retention time of 3 minutes to ease the fluctuation of the flow rate in the buffer tank 5, and the lower boiling point component (3A) was fed at a constant flow rate to the distillation column 6.

The composition of the lower boiling point component (3A) to be fed to the distillation column 6 was as follows: methyl iodide (91% by weight), methyl acetate (7% by weight), acetic acid (1% by weight), water (0.3% by weight), acetaldehyde (0.1% by weight), and hydrogen iodide (0.001% by weight).

Moreover, about 80% by volume of the higher boiling point component (4B) separated in the distillation column 6 was recycled to the reactor 1 through the buffer tank 7, and about 20% by volume of thereof was recycled to the distillation column 6 through the buffer tank 7. The flow rate of the higher boiling point component (4B) to be recycled to the distillation column 6 was constant. Moreover, although the variation in the flow rate of the higher boiling point component (4B) separated from the distillation column 6 was about ±4%, the flow rate of the higher boiling point component (4B) to be recycled through the line 23 was successfully maintained substantially constant by recycling the component (4B) through buffer tank 7.

The above-mentioned process was carried out continuously, and the process was successfully operated stably.

Comparative Example 1

The process was conducted in the same manner as in Example 2 except that the lower boiling point component (3A) of the lower layer was wholly fed to the distillation column 6 through the lines 18b to 19 and that the total amount of the higher boiling point component (4B) was recycled to the reactor 1 without going through the buffer tank 7. The liquid level of the lower layer of the decanter 4 or the flow rate of the lower boiling point component (3A) to be fed to the distillation column 6 fluctuated largely, and it was difficult to continue the stable operation in the splitter column 3 and the distillation column 6. Accordingly, the operation had to be discontinued.

Comparative Example 2

The process was conducted in the same manner as in Example 3 except that the lower boiling point component (3A) of the upper layer was wholly fed to the distillation column 6 through the lines 17b to 19 without going through the buffer tank 5 and that the higher boiling point component (4B) was recycled without going through the buffer tank 7 (about 10% by volume thereof was recycled to the reactor 1, about 20% by volume thereof was recycled to the distillation column 6, and the rest was recycled to the splitter column 3). The liquid level of the upper layer of the decanter 4 or the flow rate of the lower boiling point component (3A) to be fed to the distillation column 6 fluctuated largely, and it was difficult to continue the stable operation in the splitter column 3 and the distillation column 6. Accordingly, the operation had to be discontinued.

Comparative Example 3

The acetic acid production process was carried out in the same manner as in Example 2 except that 57% by volume of the lower boiling point component (3A) of the lower layer was fed to the line 19 (or the line 18b) without changing the flow rate of the line 18a in response to the flow rate fluctuation of the lower boiling point component (3A) to be discharged from the decanter 4. The variation in the flow rate of the lower boiling point component (3A) fed to the line 19 was in the range of 57±5% by volume.

In the distillation column 6 (a distillation column having 80 plates, reflux ratio: 170, feeding plate: the 70th plate from the top, column top temperature: 53 to 55° C., column bottom temperature: 82° C.), 0.3% by volume of the lower boiling point component (3A) was withdrawn as the lower boiling point component (4A) from the column top, and the whole amount of the residue was recycled as the higher boiling point component (4B) to the reactor 1 from the column bottom without going through the buffer tank 7. The composition of the lower boiling point component (4A) withdrawn from the column top was as follows: methyl iodide (37 to 49% by weight), water (about 1% by weight), and acetaldehyde (50 to 62% by weight).

Moreover, the lower boiling point component (4A) withdrawn from the column top was subjected to water extraction in the extractor 8, so that acetaldehyde was removed, and a raffinate containing methyl iodide was separated. Then the raffinate was divided into two fractions; one fraction was directly recycled to the bottom (10th plate) of the distillation column 6 and the other was directly recycled to the reactor 1.

The amount to be recycled to the distillation column 6 was set to constant. The acetaldehyde extraction rate of the lower boiling point component (4A) was 98%. Acetaldehyde (17 to 21 kg/hr) was successfully removed by treating the whole liquid (34 kg/hr) withdrawn from the column top of the above-mentioned distillation column having 80 plates. In this way, 53 to 66% of the acetaldehyde (32 kg/hr) produced in the reactor was successfully removed.

The above-mentioned process was carried out continuously, and the process slightly fluctuated. After the operation was carried out for a predetermined time (200 hours), the acetaldehyde concentration measured in the reactor varied from 350 to 435 ppm. It was found that the permanganate time of the resulting product acetic acid was reduced to 200 minutes.

INDUSTRIAL APPLICABILITY

The production process of the present invention is extremely useful as a process for stably producing acetic acid while efficiently separating and removing acetaldehyde.

DESCRIPTION OF REFERENCE NUMERALS

1 . . . Reactor
2 . . . Flasher (Evaporator)
3 . . . Splitter column
4 . . . Decanter
4A . . . Decanter having buffering function
5, 7 . . . Buffer tank
6 . . . Acetaldehyde separation column
8 . . . Extraction apparatus
9 . . . Hold tank

The invention claimed is:

1. A process for producing acetic acid, which comprises:
a reaction step for continuously allowing methanol to react with carbon monoxide in the presence of a catalyst system comprising a metal catalyst, a halide salt, and methyl iodide in a carbonylation reactor,
a flash evaporation step for continuously feeding a flasher with a reaction mixture from the reactor and separating a lower boiling point component (2A) containing product acetic acid and methyl iodide and a higher boiling point component (2B) containing the metal catalyst and the halide salt,
an acetic acid collection step for continuously feeding a distillation column with the lower boiling point component (2A), and separating a lower boiling point component (3A) containing methyl iodide and by-product acetaldehyde and a stream (3B) containing acetic acid to collect acetic acid,
a condensation step for condensing and temporarily holding the lower boiling point component (3A) in a decanter and discharging the lower boiling point component (3A) from the decanter, and
a separation and recycling step for separating the lower boiling point component (3A) discharged from the decanter into acetaldehyde and a liquid residue and recycling the liquid residue to a step from the reaction step to the acetaldehyde-separation step,
wherein in the condensation step, the amount of the lower boiling point component (3A) to be held is adjusted or controlled based on a fluctuating flow rate of the lower boiling point component (3A) to be fed to the decanter, and the amount of the lower boiling point component (3A) to be fed to the separation and recycling step is adjusted or controlled.

2. A process according to claim 1, wherein assuming that the average flow rate of the lower boiling point component (3A) to be fed to the decanter is 100 in terms of liquid volume, the flow rate of the lower boiling point component (3A) to be fed to the decanter is 80 to 120 in the process operation.

3. A process according to claim 1, wherein in the condensation step, the amount of the lower boiling point component (3A) to be held is adjusted by the following method (1) and/or (2):
(1) assuming that each of the average liquid level and the average interface level of the lower boiling point component (3A) to be held in the decanter is 100, the lower boiling point component (3A) is discharged from the decanter so as to adjust the liquid level and/or the interface level of the lower boiling point component (3A) to be held in the decanter to 90 to 110 in the process operation,
(2) in the condensation step, a decanter having a buffering function is used as the decanter, and the retention time of the lower boiling point component (3A) in the decanter is regulated so as to be not less than 1 minute.

4. A process according to claim 1, wherein in the condensation step, the amount of the lower boiling point component (3A) to be fed to the separation and recycling step is adjusted or controlled by at least one method selected from the group consisting of the following methods (a), (b) and (c):
(a) a method for circulating part of the lower boiling point component (3A) discharged from the decanter to a step different from the separation and recycling step,
(b) a method for feeding the separation and recycling step with the lower boiling point component (3A) discharged from the decanter through a storage vessel having a buffering function,
(c) a method for adjusting the amount of the lower boiling point component (3A) to be discharged from the decanter in the process operation to 95 to 105, assuming that the average flow rate of the lower boiling point component (3A) to be discharged from the decanter is 100.

5. A process according to claim 4, wherein in the method (a), not less than 10% of the average flow rate of the lower boiling point component (3A) to be fed to the decanter is circulated.

6. A process according to claim 4, wherein in the method (a), not less than 20% of the average flow rate of the lower boiling point component (3A) to be fed to the decanter is circulated.

7. A process according to claim 4, wherein in the method (a), 40 to 90% of the average flow rate of the lower boiling point component (3A) to be fed to the decanter is circulated.

8. A process according to claim 4, wherein in the method (a), the lower boiling point component (3A) is separated into an upper layer and a lower layer in the decanter, and the upper layer and/or the lower layer is circulated.

9. A process according to claim 4, wherein in the method (b), the retention time of the lower boiling point component (3A) in the storage vessel is not less than 0.5 minutes.

10. A process according to claim 4, wherein in the method (b), the total time of the retention time of the lower boiling point component (3A) in the decanter and the retention time of the lower boiling point component (3A) in the storage vessel is not less than 1.5 minutes.

11. A process according to claim 4, wherein in the method (c), a decanter having a buffering function is used as the decanter, and the retention time of the lower boiling point component (3A) in the decanter may be not less than 1 minute.

12. A process according to claim 1, wherein in the separation and recycling step, the lower boiling point component (3A) is fed to an acetaldehyde separation column and separated into a lower boiling point component (4A) containing acetaldehyde and a higher boiling point component (4B), as the liquid residue for recycling, containing methyl iodide by distillation.

13. A process according to claim 1, wherein in the separation and recycling step, the liquid residue is recycled through a storage vessel having a buffering function.

14. A process according to claim 12, wherein in the separation and recycling step, the lower boiling point component (4A) also contains methyl iodide, and methyl iodide is collected from the lower boiling point component (4A) for recycling.

* * * * *